(12) United States Patent
Audonnet et al.

(10) Patent No.: US 6,914,134 B2
(45) Date of Patent: Jul. 5, 2005

(54) FELINE CALICIVIRUS GENES AND VACCINES IN PARTICULAR RECOMBINANT VACCINES

(75) Inventors: Jean-Christophe Francis Audonnet, Lyons (FR); Philippe Guy Nicolas Baudu, Craponne (FR); Sylvie Claudine Brunet, Lyons (FR)

(73) Assignee: Merial, Lyons (FR)

( * ) Notice: Subject to any disclaimer, the term of this patent is extended or adjusted under 35 U.S.C. 154(b) by 0 days.

(21) Appl. No.: 10/209,507

(22) Filed: Jul. 30, 2002

(65) Prior Publication Data

US 2003/0109033 A1 Jun. 12, 2003

Related U.S. Application Data

(62) Division of application No. 09/617,594, filed on Jul. 14, 2000, now Pat. No. 6,541,458.
(60) Provisional application No. 60/193,332, filed on Mar. 30, 2000.

(30) Foreign Application Priority Data

Jul. 16, 1999 (FR) .............................................. 99 09421
Feb. 11, 2000 (FR) .............................................. 00 01761

(51) Int. Cl.$^7$ ........................ C07H 21/00; A61K 39/12
(52) U.S. Cl. ................ 536/23.1; 424/202.1; 424/204.1; 424/208.1; 435/320.1
(58) Field of Search ........................... 424/184.1, 185.1, 424/186.1, 188.1, 199.1, 202.1, 204.1, 208.1; 435/320.1; 530/300, 350; 536/23.1; 514/44

(56) References Cited

U.S. PATENT DOCUMENTS

| 5,679,356 A | 10/1997 | Bonnem et al. |
| 5,716,822 A | 2/1998 | Wardley et al. |
| 5,858,373 A | 1/1999 | Paoletti et al. |
| 5,910,488 A | 6/1999 | Nabel et al. |
| 5,951,988 A | 9/1999 | Littel-van den Hurk et al. |
| 5,989,561 A | 11/1999 | Paoletti et al. |
| 6,541,458 B1 * | 4/2003 | Audonnet et al. ............ 514/44 |

FOREIGN PATENT DOCUMENTS

| EP | 0 737 750 | 10/1996 |
| EP | 786 518 | 7/1997 |
| WO | WO 91/01332 | 7/1991 |
| WO | WO 94/16716 | 8/1994 |
| WO | WO 96/39177 | 12/1996 |
| WO | WO 98/03660 | 1/1998 |
| WO | WO 98/21354 | 5/1998 |
| WO | WO 98/56929 | 12/1998 |

OTHER PUBLICATIONS

Lauritzen, A. et al., "Serological analysis of feline calcivirus isolates from the United States and United Kingdom." Veterinary Microbiology 1997 56:55–63.

Yokoyama, N. et al., "Further development of a recombinant feline herpesvirus type 1 vector expressing feline calicivirus immunogenic antigen." J. Vet. Med. Sci. 1998 60(6):717–723.

DeSilver, D.A. et al., "Expression of the complete capsid and the hypervariable region of feline calicivirus in the baculovirus expression system." Proc. 1$^{st}$ Int. Symp. Caliciviruses ESVV 1997 pp. 131–143.

Glenn, M.A. et al., "Feline claicivirus strain F65–capsid gene sequence and implications for pathogenicity." Proc, 1$^{st}$ Int. Symp. Caliciviruses ESVV 1997 pp. 106–110.

Geissler, K. et al., "Genetic and antigenic heterogeneity among feline calicivirus isolates form distinct disease manifestations." Virus Research 1997 48:193–206.

Neill, J.D. et al., "Structure/function studies of the capsid protein of caliciviruses: domain swaps between different feline calicivirus strains." Proc. 1$^{st}$ Int. Symp. Caliciviruses ESVV 1997 pp. 120–124.

Poulet, H. et al., "Comparison between acute oral/respiratory and chronic stomatitis/gingivitis isolates of feline calicivirus: pathogenicity, antigenic profile and cross–neutralisation studies." Arch Virol. 2000 145(2):243–61.

Genbank Accession No. Z11536. Feline calicivirus genes for non structural polyprotein, viral capsid protein precursor, and two unknown ORFs. Dec. 9, 1991.

Geissler, K. et al., "Feline calicivirus capsid protein expression and capsid assembly in cultured feline cells." Journal of Virology Jan. 1999 73(1):834–838.

Guiver, M. et al., "The cloning sequencing and expression of a major antigenic region form the feline calicvirus capsid protein." Journal of General Virology Sep. 1992; 73 (Pt 9):2429–33.

Green, K. Y., et al., "expression and self–assembly of recombinant capsid protein from the antigenically distinct Hawaii human calicivirus." Journal of Clinical Microbiology Jul. 1997; 35(7):1909–1914.

Genbank Accession No. M86379, "Feline calicivirus, complete genome." Oct. 16, 1995.

Genbank Accession No. U07130, "Feline claicivirus 255 capsid protein and putative nucleic acid binding protein genes, complete cds, and polymerase gene, partial cds." Aug. 16, 1995.

Genbank Accession No. 32819, "Feline calicivirus capsid protein gene (put.), complete cds." Aug. 2, 1993.

(Continued)

Primary Examiner—Stacy B. Chen
(74) Attorney, Agent, or Firm—Frommer Lawrence & Hang; Thomas J. Kowalski; Judy Jarecki-Black

(57) ABSTRACT

The invention relates to the sequence of the capsid gene and a corresponding cDNA sequence, of a dominant FCV strain called FCV 431. It also relates to the sequence of the capsid gene as well as the cDNA sequence of a complementary strain called G1. The cDNA sequences may be incorporated into expression vectors for the preparation of immunogenic preparations and of recombinant or subunit vaccines allowing vaccination against feline calicivirosis.

24 Claims, 11 Drawing Sheets

OTHER PUBLICATIONS

Genbank Accession No. U13992, "Feline calicivirus CFI/69 RNA helicase/cysteine protease/RNA–dependent RNA polymerase polyprotein precursor and capsid protein precursor, genes, complete cds; and unknown gene." Apr. 17, 1998.

Genbank Accession No. L09719, "Feline calicivirus capsid protein gene, complete cds." Mar. 7, 1994.

Genbank Accession No. U07131, "Feline calicivirus LLK capsid protein and putative nucleic acid binding protein genes, complete cds, and polymerase gene, partial cds." Aug. 16, 1995.

Genbank Accession No. L09718, "Feline calicivirus capsid protein gene, complete cds." Mar. 7, 1994.

Genbank Accession No. X99445, "Feline calicivirus gene encoding capsid protein precursor, strain 2280." Nov. 18, 1997.

Tohya, U. et al., "Neutralizing epitopes of feline calicivirus." Archives of Virology 1991 117:173–181.

Sosnovtsev, S. and Green, K. Y. "RNA transcripts derived from a cloned full–length copy of the feline calicivirus genome do not require VpG for infectivity." Virology 1995 210:383–390.

Tartgalia et al.; "Protection of Cats Against Feline Leukemia Virus By Vaccination With A Canarypox Virus Recombinant, ALVAC–FL"; Journal of Virology, U.S., New York, vol. 67, Apr. 4, 1993, pp. 2370–2375, XP002916084.

Paoletti, E.; "Applications Of Poxvirus Vectors To Vaccination: An Update.", Proceedings of the National Academy of Sciences of the United States of America 1996, vol. 83, No. 21, 1996, pp 11349–11353, XP00213543.

* cited by examiner

| | | | | | |
|---|---|---|---|---|---|
| AAGCTTCTAT | CAAAAGTCTT | AATGAGTTAG | GTGTAGATAG | TATAGATATT | ACTACAAAGG | 60 |
| TATTCATATT | TCCTATCAAT | TCTAAAGTAG | ATGATATTAA | TAACTCAAAG | ATGATGATAG | 120 |
| TAGATAATAG | ATACGCTCAT | ATAATGACTG | CAAATTTGGA | CGGTTCACAT | TTTAATCATC | 180 |
| ACGCGTTCAT | AAGTTTCAAC | TGCATAGATC | AAAATCTCAC | TAAAAGATA | GCCGATGTAT | 240 |
| TTGAGAGAGA | TTGGACATCT | AACTACGCTA | AAGAAATTAC | AGTTATAAAT | AATACATAAT | 300 |
| GGATTTTGTT | ATCATCAGTT | ATATTTAACA | TAAGTACAAT | AAAAGTATT | AATAAAAT | 360 |
| ACTTACTTAC | GAAAAATGT | CATTATTACA | AAACTATAT | TTTACAGAAC | AATCTATAGT | 420 |
| AGAGTCCTTT | AAGAGTTATA | ATTTAAAAGA | TAACCATAAT | GTAATATTTA | CCACATCAGA | 480 |
| TGATGATACT | GTTGTAGTAA | TAAATGAAGA | TAATGTACTG | TTATCTACAA | GATTATTATC | 540 |
| ATTTGATAAA | ATTCTGTTT | TTAACTCCTT | TAATAACGGT | TTATCAAAT | ACGAAACTAT | 600 |
| TAGTGATACA | ATATTAGATA | TAGATACTCA | TAATTATTAT | ATACCTAGTT | CTTCTTCTTT | 660 |
| GTTAGATATT | CTAAAAAAA | GAGCGTGTGA | TTTAGAATTA | GAAGATCTAA | ATTATGCGTT | 720 |
| AATAGGAGAC | AATAGTAACT | TATATTATAA | AGATATGACT | TACATGAATA | ATTGGTTATT | 760 |
| TACTAAAGGA | TTATTAGATT | ACAAGTTTGT | ATTATTGCGC | GATGTAGATA | AATGTTACAA | 840 |
| ACAGTATAAT | AAAAAGAACA | CTATAATAGA | TATAATACAT | CGCGATAACA | GACAGTACAA | 900 |
| CATATGGGTT | AAAAATGTTA | TAGAATACTG | TTCTCCTGGC | TATATATTAT | GGTTACATGA | 960 |
| TCTAAAAGCC | GCTGCTGAAG | ATGATTGGTT | AAGATACGAT | AACCGTATAA | ACGAATTATC | 1020 |
| TGCGGATAAA | TTATACACTT | TCGAGTTCAT | AGTTATATTA | GAAAATAATA | TAAAACATTT | 1080 |
| ACGAGTAGGT | ACAATAATTG | TACATCCAAA | CAAGATAATA | GCTAATGGTA | CATCTAATAA | 1140 |
| TATACTTACT | GATTTTCTAT | CTTACGTAGA | AGAACTAATA | TATCATCATA | ATTCATCTAT | 1200 |
| AATATTGGCC | GGATATTTT | TAGAATTCTT | TGAGACCACT | ATTTATCAG | AATTTATTTC | 1260 |
| TTCATCTTCT | GAATGGGTAA | TGAATAGTAA | CTGTTTAGTA | CACCTGAAAA | CAGGGTATGA | 1320 |

Figure 4 (continued)

```
AGCTATACTC TTTGATGCTA GTTTATTTTT CCAACTCTCT ACTAAAAGCA ATTATGTAAA    1380
ATATTGGACA AAGAAAACTT TGCAGTATAA GAACTTTTTT AAAGACGGTA AACAGTTAGC    1440
AAAATATATA ATTAAGAAAG ATAGTCAGGT GATAGATAGA GTATGTTATT TACACGCAGC    1500
TGTATATAAT CACGTAACTT ACTTAATGGA TACGTTTAAA ATTCCTGGTT TTGATTTTAA    1560
ATTCTCCGGA ATGATAGATA TACTACTGTT TGGAATATTG CATAAGGATA ATGAGAATAT    1620
ATTTTATCCG AAACGTGTTT CTGTAACTAA TATAATATCA GAATCTATCT ATGCAGATTT    1680
TTACTTTATA TCAGATGTTA ATAAATTCAG TAAAAGATA GAATACAAA CTATGTTTCC      1740
TATACTCGCA GAAAACTACT ATCCAAAAGG AAGGCCCTAT TTTACACATA CATCTAACGA    1800
AGATCTTCTG TCTATCTGTT TATGCGAAGT AACAGTTTGT AAAGATATAA AAAATCCACT    1860
ATTATATTCT AAAAAGGATA TATCAGCAAA ACGATTCATA GGTTTATTTA CATCTGTCGA    1920
TATAAATACG GCTGTTGAGT TAAGAGGATA TAAAATAAGA GTAATAGGAT GTTTAGAATG    1980
GCCTGAAAAG ATAAAATAT TTAATTCTAA TCCTACATAC ATTAGATTAT TACTAACAGA     2040
AAGACGTTTA GATATTCTAC ATTCCTATCT GCTTAAATTT AATATAACAG AGGATATAGC    2100
TACCAGAGAT GGAGTCAGAA ATAATTTACC TATAATTTCT TTTATCGTCA GTTATTGTAG    2160
ATCGTATACT TATAAAATAC TAAATTGCCA TATGTACAAT TCGTGTAAGA TAACAAAGTG    2220
TAAATATAAT CAGGTAATAT ATAATCCTAT ATAGGAGTAT ATATAATTGA AAAAGTAAAA    2280
TATAAATCAT ATAATAATGA AACGAAATAT CAGTAATAGA CAGGAACTGG CAGATTCTTC    2340
TTCTAATGAA GTAAGTACTG CTAAATCTCC AAAATTAGAT AAAATGATA CAGCAAATAC     2400
AGCTTCATTC AACGAATTAC CTTTTAATTT TTTCAGACAC ACCTTACTAC AAACTAACTA    2460
AGTCAGATGA TGAGAAAGTA AATATAAATT TAACTTATGG GTATAATATA ATAAAGATTC    2520
ATGATATTAA TAATTTACTT AACGATGTTA ATAGACTTAT TCCATCAACC CCTTCAAACC    2580
TTTCTGGATA TTATAAAACA CCAGTTAATG ATATTAAAAT AGATTGTTTA AGAGATGTAA    2640
ATAATTATTT GGAGGTAAAG GATATAAAAT TAGTCTATCT TTCACATGGA AATGAATTAC    2700
CTAACATTAA TAATTATGAT AGGAATTTTT TAGGATTTAC AGCTGTTATA TGTATCAAACA   2760
```

Figure 4 (continued and end)

```
ATACAGGCAG ATCTATGGTT ATGGTAAAAC ACTGTAACGG GAAGCAGCAT TCTATGGTAA    2820
CTGGCCTATG TTTAATAGCC AGATCATTTT ACTCTATAAA CATTTTACCA CAAATAATAG    2880
GATCCTCTAG ATATTTAATA TTATATCTAA CAACAACAAA AAAATTTAAC GATGTATGGC    2940
CAGAAGTATT TTCTACTAAT AAAGATAAAG ATAGTCTATC TTATCTACAA GATATGAAAG    3000
AAGATAATCA TTTAGTAGTA GCTACTAATA TGGAAAGAAA TGTATACAAA AACGTGGAAG    3060
CTTTTATATT AAATAGCATA TTACTAGAAG ATTTAAAATC TAGACTTAGT ATAACAAAAC    3120
AGTTAAATGC CAATATCGAT TCTATATTTC ATCATAACAG TAGTACATTA ATCAGTGATA    3180
TACTGAAACG ATCTACAGAC TCAACTATGC AAGGAATAAG CAATATGCCA ATTATGTCTA    3240
ATATTTTAAC TTTAGAACTA AAACGTTCTA CCAATACTAA AAATAGGATA CGTGATAGGC    3300
TGTTAAAAGC TGCAATAAAT AGTAAGGATG TAGAAGAAAT ACTTTGTTCT ATACCTTCGG    3360
AGGAAAGAAC TTTAGAACAA CTTAAGTTTA ATCAAACTTG TATTTATGAA CACTATAAAA    3420
AAATTATGGA AGATACAAGT AAAAGAATGG ATGTTGAATG TCGTAGTTTA GAACATAACT    3480
ATACGGCTAA CTTATATAAA GTGTACGGAC AAAACGAATA TATGATTACT TATATACTAG    3540
CTCTCATAAG TAGGATTAAT AATATTATAG AAATTTAAA ATATAATCTG GTGGGCTAG    3600
ACGAATCTAC AATACGTAAT ATAAATTATA TAATTCACA AAGAACAAAA AAAAATCAAG    3660
TTTCTAAAAC CTTACAGATA AACTATATTT TTTACCACTG A                       3701
```

Figure 6

```
1909 ATG TGG CTG CAG AAC CTG CTT TTC CTG GGC ACT GTG GTC TGC AGC ATC TCT GCA CCC
     TAC ACC GAC GTC TTG GAC GAA AAG GAC CCG TGA CAC CAG ACG TCG TAG AGA CGT GGG
   1▸Met Trp Leu Gln Asn Leu Leu Phe Leu Gly Thr Val Val Cys Ser Ile Ser Ala Pro

1966 ACC AGT TCA CCC AGC TCT GTC ACT CGG CCC TGG CAA CAC GTG GAT GCC ATC AAG GAG
     TGG TCA AGT GGG TCG AGA CAG TGA GCC GGG ACC GTT GTG CAC CTA CGG TAG TTC CTC
  20▸Thr Ser Ser Pro Ser Ser Val Thr Arg Pro Trp Gln His Val Asp Ala Ile Lys Glu

2023 GCT CTG AGC CTT CTG AAC AAC AGT AGT GAA ATA ACT GCT GTG ATG AAT GAA GCA GTA
     CGA GAC TCG GAA GAC TTG TTG TCA TCA CTT TAT TGA CGA CAC TAC TTA CTT CGT CAT
  39▸Ala Leu Ser Leu Leu Asn Asn Ser Ser Glu Ile Thr Ala Val Met Asn Glu Ala Val

2080 GAA GTC GTC TCT GAA ATG TTT GAC CCT GAG GAG CCG AAA TGC CTG CAG ACT CAC CTA
     CTT CAG CAG AGA CTT TAC AAA CTG GGA CTC CTC GGC TTT ACG GAC GTC TGA GTG GAT
  58▸Glu Val Val Ser Glu Met Phe Asp Pro Glu Glu Pro Lys Cys Leu Gln Thr His Leu

2137 AAG CTG TAC GAG CAG GGC CTA CGG GGC AGC CTC ATC AGC CTC AAG GAG CCT CTG AGA
     TTC GAC ATG CTC GTC CCG GAT GCC CCG TCG GAG TAG TCG GAG TTC CTC GGA GAC TCT
  77▸Lys Leu Tyr Glu Gln Gly Leu Arg Gly Ser Leu Ile Ser Leu Lys Glu Pro Leu Arg

2194 ATG ATG GCC AAC CAT TAC AAG CAG CAC TGC CCC TTT ACT CCG GAA ACG CCC TGT GAA
     TAC TAC CGG TTG GTA ATG TTC GTC GTG ACG GGG AAA TGA GGC CTT GCG GGA ACA CTT
  96▸Met Met Ala Asn His Tyr Lys Gln His Cys Pro Phe Thr Pro Glu Thr Pro Cys Glu

2251 ACC CAG ACT ATC ACC TTC AAA AAT TTC AAA GAG AAT CTG AAG GAT TTT CTG TTT AAC
     TGG GTC TGA TAG TGG AAG TTT TTA AAG TTT CTC TTA GAC TTC CTA AAA GAC AAA TTG
 115▸Thr Gln Thr Ile Thr Phe Lys Asn Phe Lys Glu Asn Leu Lys Asp Phe Leu Phe Asn

2308 ATC CCC TTT GAC TGC TGG AAA CCA GTC AAG AAG TGA
     TAG GGG AAA CTG ACG ACC TTT GGT CAG TTC TTC ACT
 134▸Ile Pro Phe Asp Cys Trp Lys Pro Val Lys Lys •••
```

Figure 8

```
1909 ATG TGG CTG CAG AAC CTG CTT TTC CTG GGC ACT GTG GTC TGC AGC ATC TCT GCA CCC
     TAC ACC GAC GTC TTG GAC GAA AAG GAC CCG TGA CAC CAG ACG TCG TAG AGA CGT GGG
   1▶Met Trp Leu Gln Asn Leu Leu Phe Leu Gly Thr Val Val Cys Ser Ile Ser Ala Pro

1966 ACC AGT TCA CCC AGC TCT GTC ACT CGG CCC TGG CAA CAC GTG GAT GCC ATC AAG GAG
     TGG TCA AGT GGG TCG AGA CAG TGA GCC GGG ACC GTT GTG CAC CTA CGG TAG TTC CTC
  20▶Thr Ser Ser Pro Ser Ser Val Thr Arg Pro Trp Gln His Val Asp Ala Ile Lys Glu

2023 GCT CTG AGC CTT CTG AAC AAC AGT AGT GAA ATA ACT GCT GTG ATG AAT GAA GCA GTA
     CGA GAC TCG GAA GAC TTG TTG TCA TCA CTT TAT TGA CGA CAC TAC TTA CTT CGT CAT
  39▶Ala Leu Ser Leu Leu Asn Asn Ser Ser Glu Ile Thr Ala Val Met Asn Glu Ala Val

2080 GAA GTC GTC TCT GAA ATG TTT GAC CCT GAG GAG CCG AAA TGC CTG CAG ACT CAC CTA
     CTT CAG CAG AGA CTT TAC AAA CTG GGA CTC CTC GGC TTT ACG GAC GTC TGA GTG GAT
  58▶Glu Val Val Ser Glu Met Phe Asp Pro Glu Glu Pro Lys Cys Leu Gln Thr His Leu

2137 AAG CTG TAC GAG CAG GGC CTA CGG GGC AGC CTC ATC AGC CTC AAG GAG CCT CTG AGG
     TTC GAC ATG CTC GTC CCG GAT GCC CCG TCG GAG TAG TCG GAG TTC CTC GGA GAC TCC
  77▶Lys Leu Tyr Glu Gln Gly Leu Arg Gly Ser Leu Ile Ser Leu Lys Glu Pro Leu Arg

2194 ATG ATG GCC AAC CAT TAC AAG CAG CAC TGC CCC CTT ACT CCG GAA ACG CCC TGT GAA
     TAC TAC CGG TTG GTA ATG TTC GTC GTG ACG GGG GAA TGA GGC CTT TGC GGG ACA CTT
  96▶Met Met Ala Asn His Tyr Lys Gln His Cys Pro Leu Thr Pro Glu Thr Pro Cys Glu

2251 ACC CAG ACT ATC ACC TTC AAA AAT TTC AAA GAG AAT CTG AAG GAT TTT CTG TTT AAC
     TGG GTC TGA TAG TGG AAG TTT TTA AAG TTT CTC TTA GAC TTC CTA AAA GAC AAA TTG
 115▶Thr Gln Thr Ile Thr Phe Lys Asn Phe Lys Glu Asn Leu Lys Asp Phe Leu Phe Asn

2308 ATC CCC TTT GAC TGC TGG AAA CCA GTC AAG AAG TGA
     TAG GGG AAA CTG ACG ACC TTT GGT CAG TTC TTC ACT
 134▶Ile Pro Phe Asp Cys Trp Lys Pro Val Lys Lys ···
```

Figure 9

| Isolate/serum | SrA2 | SrF1 | SrG1 | SrH3-2 | SrG3 | rF300 | SrH1-4 | Sr3890 | SrD1 | Sr337 | SrJ5 | SrRM11 | SrRM12 | SrRM13 | SrRM15 | SrRM16 | SrRM17 | SrRM19 | Sr255 | SrF9 |
|---|---|---|---|---|---|---|---|---|---|---|---|---|---|---|---|---|---|---|---|---|
| A2 (FR) | 3.5 | 0.8 | 2.5 | 1.2 | 1.0 | 1.8 | 1.3 | 0.7 | 0.8 | 1.1 | 0.9 | 0.7 | 0.7 | 0.7 | 2.0 | 1.2 | 0.7 | 1.7 | 1.2 | 1.8 |
| F1 (FR) | 1.2 | 3.0 | 2.2 | 1.9 | 0.9 | 1.1 | 1.0 | 1.9 | 1.3 | 0.7 | 0.7 | 0.7 | 0.7 | 0.7 | 0.7 | 0.7 | 0.7 | 0.7 | 0.7 | 1.0 |
| G1 (FR) | 1.6 | 0.8 | 2.9 | 1.2 | 1.0 | 1.7 | 0.7 | 0.9 | 2.6 | 0.7 | 0.8 | 0.7 | 0.7 | 0.7 | 0.9 | 0.7 | 0.7 | 0.7 | 1.3 | 1.1 |
| H3-2 (FR) | 0.7 | 0.7 | 0.7 | 2.8 | 0.7 | 0.7 | 0.9 | 0.9 | 1.3 | 0.7 | 1.1 | 1.1 | 0.7 | 0.7 | 0.7 | 0.7 | 0.7 | 0.7 | 0.7 | 0.7 |
| G3 (FR) | 1.0 | 1.1 | 2.4 | 1.7 | 3.5 | 1.6 | 1.3 | 0.8 | 1.8 | 0.7 | 0.7 | 0.7 | 0.7 | 0.7 | 0.7 | 0.7 | 0.7 | 1.2 | 0.8 | 0.7 |
| F3031 (FR) | 2.4 | 1.5 | 2.0 | 1.7 | 1.2 | 3.8 | 1.1 | 0.9 | 2.0 | 0.7 | 1.2 | 0.8 | 0.7 | 0.7 | 0.7 | 1.0 | 0.7 | 0.7 | 1.1 | 2.0 |
| H1-4 (FR) | 0.7 | 0.7 | 1.1 | 1.2 | 0.7 | 0.7 | 3.2 | 1.2 | 1.3 | 0.7 | 1.0 | 0.7 | 0.7 | 0.7 | 0.7 | 1.1 | 0.7 | 1.2 | 0.7 | 0.7 |
| 3890 (UK) | 0.7 | 0.7 | 0.7 | 0.7 | 0.7 | 0.7 | 0.7 | 3.1 | 2.1 | 1.0 | 0.9 | 0.7 | 0.7 | 0.7 | 0.7 | 0.7 | 1.0 | 0.7 | 0.7 | 2.0 |
| 431 (UK) | 0.7 | 0.7 | 0.9 | 0.7 | 0.7 | 0.7 | 0.8 | 1.1 | 3.5 | 3.2 | 1.2 | 0.7 | 0.7 | 0.7 | 0.8 | 0.7 | 0.7 | 0.7 | 0.8 | 0.7 |
| 337 (UK) | 1.0 | 0.7 | 1.1 | 0.7 | 0.7 | 0.9 | 1.1 | 1.1 | 2.2 | 0.7 | 1.3 | 2.7 | 2.3 | 0.7 | 0.7 | 1.0 | 0.7 | 1.8 | 0.9 | 0.7 |
| J5 (UK) | 0.7 | 0.7 | 1.0 | 0.7 | 0.7 | 0.7 | 0.7 | 0.7 | 1.6 | 0.7 | 1.0 | 0.7 | 2.2 | 0.7 | 0.7 | 1.3 | 1.3 | 1.2 | 0.7 | 0.7 |
| RM11 (US) | 0.7 | 0.7 | 1.0 | 1.2 | 0.7 | 0.7 | 0.7 | 1.1 | 1.4 | 0.7 | 1.3 | 2.6 | 0.7 | 3.1 | 0.7 | 1.3 | 1.8 | 0.7 | 0.7 | 0.7 |
| RM12 (US) | 0.7 | 0.7 | 1.0 | 0.7 | 0.7 | 0.7 | 0.7 | 0.7 | 1.5 | 0.7 | 1.0 | 0.8 | 0.7 | 0.7 | 2.4 | 1.3 | 0.7 | 2.5 | 0.7 | 0.7 |
| RM13 (US) | 1.2 | 0.7 | 1.2 | 0.7 | 0.7 | 0.7 | 0.7 | 1.3 | 1.9 | 0.7 | 0.9 | 1.1 | 0.7 | 0.7 | 0.7 | 2.5 | 0.7 | 0.7 | 0.7 | 0.7 |
| RM15 (US) | 1.2 | 0.7 | 1.1 | 0.7 | 0.7 | 1.3 | 0.7 | 1.5 | 1.0 | 0.7 | 1.4 | 0.7 | 1.2 | 0.7 | 0.8 | 2.5 | 3.0 | 2.5 | 0.7 | 0.7 |
| RM16 (US) | 1.1 | 0.7 | 1.2 | 0.7 | 0.7 | 0.7 | 0.7 | 0.7 | 1.8 | 0.7 | 0.7 | 0.7 | 0.7 | 0.7 | 0.7 | 0.7 | 0.7 | 0.7 | 0.7 | 0.7 |
| RM17 (US) | 1.1 | 0.7 | 1.2 | 0.7 | 0.9 | 0.7 | 0.7 | 0.7 | 1.0 | 0.7 | 0.7 | 0.7 | 0.7 | 0.7 | 0.7 | 2.5 | 3.0 | 2.5 | 0.7 | 0.7 |
| RM19 (US) | 1.1 | 0.7 | 1.2 | 0.7 | 0.9 | 0.7 | 0.7 | 0.7 | 1.0 | 0.7 | 0.7 | 0.7 | 0.7 | 0.7 | 0.7 | 2.5 | 0.7 | 2.4 | 0.7 | 0.7 |

SEQUENCE LISTING

<160> NUMBER OF SEQ ID NOS: 26

<210> SEQ ID NO 1
<211> LENGTH: 2010
<212> TYPE: DNA
<213> ORGANISM: Feline calicivirus
<220> FEATURE:
<221> NAME/KEY: CDS
<222> LOCATION: (1)..(2007)
<223> OTHER INFORMATION: coding sequence of the "capsid" protein of FCV
    G1 strain

<400> SEQUENCE: 1

```
atg tgc tca acc tgc gct aac gtg ctt aaa tac tat gat tgg gat ccc        48
Met Cys Ser Thr Cys Ala Asn Val Leu Lys Tyr Tyr Asp Trp Asp Pro
1               5                   10                  15 cac aca aaa ttg gtt att gac ccc aat aaa ttc ctt tct cta ggc ttc        96
His Thr Lys Leu Val Ile Asp Pro Asn Lys Phe Leu Ser Leu Gly Phe
            20                  25                  30 tgc gat aaa ccg ctt tta tgc tgc tac cca gaa ctt ctc cca gaa ttt       144
Cys Asp Lys Pro Leu Leu Cys Cys Tyr Pro Glu Leu Leu Pro Glu Phe
        35                  40                  45 gga aca gtg tgg gat tgt gac caa tcc cct cta caa att tac ctt gaa       192
Gly Thr Val Trp Asp Cys Asp Gln Ser Pro Leu Gln Ile Tyr Leu Glu
    50                  55                  60 tct atc ctt ggt gat gat gaa tgg agc tcg aca ttt gat gct atc gat       240
Ser Ile Leu Gly Asp Asp Glu Trp Ser Ser Thr Phe Asp Ala Ile Asp
65                  70                  75                  80 cct gtt gtt cct ccc atg cat tgg gac aag gct ggg aaa atc ttc cag       288
Pro Val Val Pro Pro Met His Trp Asp Lys Ala Gly Lys Ile Phe Gln
                85                  90                  95 cct cat cct ggt gtt cta atg cac cac ctc atc aat gaa gtt gca aaa       336
Pro His Pro Gly Val Leu Met His His Leu Ile Asn Glu Val Ala Lys
            100                 105                 110 gct tgg gat cca aat ctc ccc atc ttc cga ttg gaa gct gac ggg gat       384
Ala Trp Asp Pro Asn Leu Pro Ile Phe Arg Leu Glu Ala Asp Gly Asp
        115                 120                 125 tca tcc atc acg acc cct gag caa gga aca ttg gtc ggt ggt gtt att       432
Ser Ser Ile Thr Thr Pro Glu Gln Gly Thr Leu Val Gly Gly Val Ile
```

```
                    130                 135                 140
gcc gag ccc agc gct caa atg gca act gct gct gac gca gca act ggc      480
Ala Glu Pro Ser Ala Gln Met Ala Thr Ala Ala Asp Ala Ala Thr Gly
145                 150                 155                 160 aag agt gtt gac tcg gaa tgg gag tct ttc ttc tca ttc cat act agt      528
Lys Ser Val Asp Ser Glu Trp Glu Ser Phe Phe Ser Phe His Thr Ser
                    165                 170                 175 gtg aat tgg agt aca tct gaa acc cag gga aag atc ctc ttt aaa caa      576
Val Asn Trp Ser Thr Ser Glu Thr Gln Gly Lys Ile Leu Phe Lys Gln
                180                 185                 190 tct tta gga ccc cta ctt aat cct tac ctt gaa cac ctt tct aaa tta      624
Ser Leu Gly Pro Leu Leu Asn Pro Tyr Leu Glu His Leu Ser Lys Leu
            195                 200                 205 tac gtt gct tgg tct gga tca gtg gat gta agg ttc tct att tct ggc      672
Tyr Val Ala Trp Ser Gly Ser Val Asp Val Arg Phe Ser Ile Ser Gly
        210                 215                 220 tcc ggt gtc ttc ggg ggg aaa ttg gct gcc att gtt gtg cct cca ggg      720
Ser Gly Val Phe Gly Gly Lys Leu Ala Ala Ile Val Val Pro Pro Gly
225                 230                 235                 240 gtt gac ccc gtc cag agc acg tca atg ctc cag tat ccc cat gtc ctc      768
Val Asp Pro Val Gln Ser Thr Ser Met Leu Gln Tyr Pro His Val Leu
                245                 250                 255 ttt gat gct cgc caa gtt gaa cct gtt ata ttt tca atc ccc gat tta      816
Phe Asp Ala Arg Gln Val Glu Pro Val Ile Phe Ser Ile Pro Asp Leu
                260                 265                 270 agg agc act ctc tat cac cta atg tct gat act gat act aca tcc ctt      864
Arg Ser Thr Leu Tyr His Leu Met Ser Asp Thr Asp Thr Thr Ser Leu
            275                 280                 285 gtt atc atg gta tat aat gat ctt att aac cct tat gct aat gat tcc      912
Val Ile Met Val Tyr Asn Asp Leu Ile Asn Pro Tyr Ala Asn Asp Ser
        290                 295                 300 aac tct tct ggg tgt att gtt acc gtt gag acc aaa cct gga cct gac      960
Asn Ser Ser Gly Cys Ile Val Thr Val Glu Thr Lys Pro Gly Pro Asp
305                 310                 315                 320 ttc aaa ttt cac ctc ctg aaa cca cct gga tca atg tta act cat ggc     1008
Phe Lys Phe His Leu Leu Lys Pro Pro Gly Ser Met Leu Thr His Gly
                325                 330                 335 tct att ccc tct gac ttg att cca aaa tct tca tcc ctt tgg att gga     1056
Ser Ile Pro Ser Asp Leu Ile Pro Lys Ser Ser Ser Leu Trp Ile Gly
                340                 345                 350 aat cga tat tgg tct gac ata act gat ttt gta att cgg cca ttc gtg     1104
Asn Arg Tyr Trp Ser Asp Ile Thr Asp Phe Val Ile Arg Pro Phe Val
            355                 360                 365 ttt caa gcc aat cgt cac ttt gac ttc aac caa gaa acg gct gga tgg     1152
Phe Gln Ala Asn Arg His Phe Asp Phe Asn Gln Glu Thr Ala Gly Trp
        370                 375                 380 agc aca cca aga ttt cga ccc ata aca ata act att agt gaa agt aat     1200
Ser Thr Pro Arg Phe Arg Pro Ile Thr Ile Thr Ile Ser Glu Ser Asn
385                 390                 395                 400 gga tca aaa ctg gga act ggc gtg gcc aca gat tac att gtg ccc ggc     1248
Gly Ser Lys Leu Gly Thr Gly Val Ala Thr Asp Tyr Ile Val Pro Gly
                405                 410                 415 ata cct gat ggt tgg cct gac acc aca att ggt gag gaa ttg aca cca     1296
Ile Pro Asp Gly Trp Pro Asp Thr Thr Ile Gly Glu Glu Leu Thr Pro
                420                 425                 430 gct gga gat tac tca atc aca aac ggt agt ggc aat gac att gca aca     1344
Ala Gly Asp Tyr Ser Ile Thr Asn Gly Ser Gly Asn Asp Ile Ala Thr
            435                 440                 445 gct aat gct tat gac agt gct gat gtg atc aca aac acc aca aat ttc     1392
```

```
                                                                       1440
Ala Asn Ala Tyr Asp Ser Ala Asp Val Ile Thr Asn Thr Thr Asn Phe
    450             455                 460
agg ggg atg tac att tgt gga gca ctc cag agg gct tgg ggc gat aag        1440
Arg Gly Met Tyr Ile Cys Gly Ala Leu Gln Arg Ala Trp Gly Asp Lys
465             470                 475                 480 aag atc tca agt aca gct ttc ata acc act gct att aag gaa ggt aat        1488
Lys Ile Ser Ser Thr Ala Phe Ile Thr Thr Ala Ile Lys Glu Gly Asn
                485                 490                 495 acg ctt aaa cca tca aat aca att gac atg aca aaa att gct gtg tac        1536
Thr Leu Lys Pro Ser Asn Thr Ile Asp Met Thr Lys Ile Ala Val Tyr
            500                 505                 510 cag gac act cat gtt ggc agg gat gtt caa aca tct gat gat aca ctg        1584
Gln Asp Thr His Val Gly Arg Asp Val Gln Thr Ser Asp Asp Thr Leu
        515                 520                 525 gca atc ctt ggt tac act gga att ggt gaa cag gca att gga tct aat        1632
Ala Ile Leu Gly Tyr Thr Gly Ile Gly Glu Gln Ala Ile Gly Ser Asn
    530                 535                 540 agg gat agt gtg gtt cgc att agc atg ctg ccg gaa act ggt gcc cgc        1680
Arg Asp Ser Val Val Arg Ile Ser Met Leu Pro Glu Thr Gly Ala Arg
545                 550                 555                 560 ggc ggg aat cac cca att ttc tac aaa aat tct att aag tta gga tat        1728
Gly Gly Asn His Pro Ile Phe Tyr Lys Asn Ser Ile Lys Leu Gly Tyr
                565                 570                 575 gta ctc agg tca att gat gtg ttc aac tca caa att ctc cac aca tct        1776
Val Leu Arg Ser Ile Asp Val Phe Asn Ser Gln Ile Leu His Thr Ser
            580                 585                 590 aga caa ctg tcc ctc aat cat tac ttg cta cca cct gac tca ttt gct        1824
Arg Gln Leu Ser Leu Asn His Tyr Leu Leu Pro Pro Asp Ser Phe Ala
        595                 600                 605 gtt tat agg att ata gac tct aat gga tct tgg ttt gat gta ggg att        1872
Val Tyr Arg Ile Ile Asp Ser Asn Gly Ser Trp Phe Asp Val Gly Ile
    610                 615                 620 gat agt gat ggt ttt tcc ttt gtt ggt gtt tct agt atc cct aaa ctt        1920
Asp Ser Asp Gly Phe Ser Phe Val Gly Val Ser Ser Ile Pro Lys Leu
625                 630                 635                 640 gag ttt cct ctt tct gcc tcc tac atg gga att cag ctg gca aag att        1968
Glu Phe Pro Leu Ser Ala Ser Tyr Met Gly Ile Gln Leu Ala Lys Ile
                645                 650                 655 cga ctt gcc tct aac att agg agt act atg aca aaa cta tga              2010
Arg Leu Ala Ser Asn Ile Arg Ser Thr Met Thr Lys Leu
            660                 665

<210> SEQ ID NO 2
<211> LENGTH: 669
<212> TYPE: PRT
<213> ORGANISM: Feline calicivirus

<400> SEQUENCE: 2

Met Cys Ser Thr Cys Ala Asn Val Leu Lys Tyr Tyr Asp Trp Asp Pro
1               5                   10                  15

His Thr Lys Leu Val Ile Asp Pro Asn Lys Phe Leu Ser Leu Gly Phe
                20                  25                  30

Cys Asp Lys Pro Leu Leu Cys Cys Tyr Pro Glu Leu Leu Pro Glu Phe
            35                  40                  45

Gly Thr Val Trp Asp Cys Asp Gln Ser Pro Leu Gln Ile Tyr Leu Glu
        50                  55                  60

Ser Ile Leu Gly Asp Asp Glu Trp Ser Ser Thr Phe Asp Ala Ile Asp
65                  70                  75                  80

Pro Val Val Pro Pro Met His Trp Asp Lys Ala Gly Lys Ile Phe Gln
```

-continued

```
                85                  90                  95
Pro His Pro Gly Val Leu Met His His Leu Ile Asn Glu Val Ala Lys
            100                 105                 110
Ala Trp Asp Pro Asn Leu Pro Ile Phe Arg Leu Glu Ala Asp Gly Asp
            115                 120                 125
Ser Ser Ile Thr Thr Pro Glu Gln Gly Thr Leu Val Gly Gly Val Ile
            130                 135                 140
Ala Glu Pro Ser Ala Gln Met Ala Thr Ala Ala Asp Ala Ala Thr Gly
145                 150                 155                 160
Lys Ser Val Asp Ser Glu Trp Glu Ser Phe Phe Ser Phe His Thr Ser
                165                 170                 175
Val Asn Trp Ser Thr Ser Glu Thr Gln Gly Lys Ile Leu Phe Lys Gln
                180                 185                 190
Ser Leu Gly Pro Leu Leu Asn Pro Tyr Leu Glu His Leu Ser Lys Leu
                195                 200                 205
Tyr Val Ala Trp Ser Gly Ser Val Asp Val Arg Phe Ser Ile Ser Gly
            210                 215                 220
Ser Gly Val Phe Gly Gly Lys Leu Ala Ala Ile Val Val Pro Pro Gly
225                 230                 235                 240
Val Asp Pro Val Gln Ser Thr Ser Met Leu Gln Tyr Pro His Val Leu
                245                 250                 255
Phe Asp Ala Arg Gln Val Glu Pro Val Ile Phe Ser Ile Pro Asp Leu
            260                 265                 270
Arg Ser Thr Leu Tyr His Leu Met Ser Asp Thr Asp Thr Thr Ser Leu
            275                 280                 285
Val Ile Met Val Tyr Asn Asp Leu Ile Asn Pro Tyr Ala Asn Asp Ser
            290                 295                 300
Asn Ser Ser Gly Cys Ile Val Thr Val Glu Thr Lys Pro Gly Pro Asp
305                 310                 315                 320
Phe Lys Phe His Leu Leu Lys Pro Pro Gly Ser Met Leu Thr His Gly
                325                 330                 335
Ser Ile Pro Ser Asp Leu Ile Pro Lys Ser Ser Ser Leu Trp Ile Gly
            340                 345                 350
Asn Arg Tyr Trp Ser Asp Ile Thr Asp Phe Val Ile Arg Pro Phe Val
            355                 360                 365
Phe Gln Ala Asn Arg His Phe Asp Phe Asn Gln Glu Thr Ala Gly Trp
            370                 375                 380
Ser Thr Pro Arg Phe Arg Pro Ile Thr Ile Thr Ile Ser Glu Ser Asn
385                 390                 395                 400
Gly Ser Lys Leu Gly Thr Gly Val Ala Thr Asp Tyr Ile Val Pro Gly
                405                 410                 415
Ile Pro Asp Gly Trp Pro Asp Thr Thr Ile Gly Glu Glu Leu Thr Pro
            420                 425                 430
Ala Gly Asp Tyr Ser Ile Thr Asn Gly Ser Gly Asn Asp Ile Ala Thr
            435                 440                 445
Ala Asn Ala Tyr Asp Ser Ala Asp Val Ile Thr Asn Thr Thr Asn Phe
450                 455                 460
Arg Gly Met Tyr Ile Cys Gly Ala Leu Gln Arg Ala Trp Gly Asp Lys
465                 470                 475                 480
Lys Ile Ser Ser Thr Ala Phe Ile Thr Thr Ala Ile Lys Glu Gly Asn
                485                 490                 495
Thr Leu Lys Pro Ser Asn Thr Ile Asp Met Thr Lys Ile Ala Val Tyr
                500                 505                 510
```

-continued

```
Gln Asp Thr His Val Gly Arg Asp Val Gln Thr Ser Asp Asp Thr Leu
        515                 520                 525

Ala Ile Leu Gly Tyr Thr Gly Ile Gly Glu Gln Ala Ile Gly Ser Asn
    530                 535                 540

Arg Asp Ser Val Val Arg Ile Ser Met Leu Pro Glu Thr Gly Ala Arg
545                 550                 555                 560

Gly Gly Asn His Pro Ile Phe Tyr Lys Asn Ser Ile Lys Leu Gly Tyr
                565                 570                 575

Val Leu Arg Ser Ile Asp Val Phe Asn Ser Gln Ile Leu His Thr Ser
        580                 585                 590

Arg Gln Leu Ser Leu Asn His Tyr Leu Leu Pro Pro Asp Ser Phe Ala
    595                 600                 605

Val Tyr Arg Ile Ile Asp Ser Asn Gly Ser Trp Phe Asp Val Gly Ile
610                 615                 620

Asp Ser Asp Gly Phe Ser Phe Val Gly Val Ser Ser Ile Pro Lys Leu
625                 630                 635                 640

Glu Phe Pro Leu Ser Ala Ser Tyr Met Gly Ile Gln Leu Ala Lys Ile
                645                 650                 655

Arg Leu Ala Ser Asn Ile Arg Ser Thr Met Thr Lys Leu
    660                 665
```

<210> SEQ ID NO 3
<211> LENGTH: 2007
<212> TYPE: DNA
<213> ORGANISM: Feline calcivirus
<220> FEATURE:
<221> NAME/KEY: CDS
<222> LOCATION: (1)..(2004)
<223> OTHER INFORMATION: coding sequence of the "capsid" protein of FCV
      431 strain

<400> SEQUENCE: 3

```
atg tgc tca acc tgc gct aac gtg ctt aaa tac tat gat tgg gat ccc      48
Met Cys Ser Thr Cys Ala Asn Val Leu Lys Tyr Tyr Asp Trp Asp Pro
1               5                   10                  15 cac ttt aga ttg att att aac ccc aac aaa ttt ctt tcc gtt ggc ttc      96
His Phe Arg Leu Ile Ile Asn Pro Asn Lys Phe Leu Ser Val Gly Phe
            20                  25                  30 tgt gat aat cct ctt atg tgt tgt tat ccc gaa tta ctc cct gaa ttt     144
Cys Asp Asn Pro Leu Met Cys Cys Tyr Pro Glu Leu Leu Pro Glu Phe
        35                  40                  45 gga act gtg tgg gac tgt gat cag tca cca ctc caa att tat cta gag     192
Gly Thr Val Trp Asp Cys Asp Gln Ser Pro Leu Gln Ile Tyr Leu Glu
    50                  55                  60 tcc atc ctt ggt gat gac gaa tgg gct tcc act tac gaa gca gtt gac     240
Ser Ile Leu Gly Asp Asp Glu Trp Ala Ser Thr Tyr Glu Ala Val Asp
65                  70                  75                  80 cca gtg gtg cca cca atg cat tgg gat agt gct gga aag atc ttt cag     288
Pro Val Val Pro Pro Met His Trp Asp Ser Ala Gly Lys Ile Phe Gln
                85                  90                  95 cca cat cct ggt gta ttg atg cac cat ctg att ggt gaa gtt gct aag     336
Pro His Pro Gly Val Leu Met His His Leu Ile Gly Glu Val Ala Lys
            100                 105                 110 gcc tgg gat cca aac tta cca ctc ttt cgt ctg gaa gcg gat gat gga     384
Ala Trp Asp Pro Asn Leu Pro Leu Phe Arg Leu Glu Ala Asp Asp Gly
        115                 120                 125 tct gtg acc acg cct gaa caa gga aca ctg gtt ggt gga gtc att gct     432
Ser Val Thr Thr Pro Glu Gln Gly Thr Leu Val Gly Gly Val Ile Ala
    130                 135                 140
```

```
gag cct aat gcc caa atg tca gct gtt gct gac gtg gcc act ggc aaa        480
Glu Pro Asn Ala Gln Met Ser Ala Val Ala Asp Val Ala Thr Gly Lys
145                 150                 155                 160 agt gtt gac tct gag tgg gaa gca ttc ttc tct ttc cac acc agt gtc        528
Ser Val Asp Ser Glu Trp Glu Ala Phe Phe Ser Phe His Thr Ser Val
                165                 170                 175 aat tgg agc aca tct gaa acc caa ggg aaa atc ctt ttt aaa caa tct        576
Asn Trp Ser Thr Ser Glu Thr Gln Gly Lys Ile Leu Phe Lys Gln Ser
            180                 185                 190 cta ggt ccc cta ctt aac cct tac ctt act cat ctc gca aaa ctt tat        624
Leu Gly Pro Leu Leu Asn Pro Tyr Leu Thr His Leu Ala Lys Leu Tyr
        195                 200                 205 gtt gca tgg tct ggt tct att gag gtt aga ttt tca att tct gga tct        672
Val Ala Trp Ser Gly Ser Ile Glu Val Arg Phe Ser Ile Ser Gly Ser
    210                 215                 220 ggt gtc ttt ggt gga aaa ctg gct gct att gtt gtg cca ccc ggg atc        720
Gly Val Phe Gly Gly Lys Leu Ala Ala Ile Val Val Pro Pro Gly Ile
225                 230                 235                 240 gat ccc gtg caa agc aca tca atg ttg cag tac ccc cat gtt ctg ttt        768
Asp Pro Val Gln Ser Thr Ser Met Leu Gln Tyr Pro His Val Leu Phe
                245                 250                 255 gat gct cgt caa gtt gaa cct gtt atc ttc act atc cct gat ttg aga        816
Asp Ala Arg Gln Val Glu Pro Val Ile Phe Thr Ile Pro Asp Leu Arg
            260                 265                 270 aat agt cta tat cac ctt atg tct gac act gat act aca tct ctt gtc        864
Asn Ser Leu Tyr His Leu Met Ser Asp Thr Asp Thr Thr Ser Leu Val
        275                 280                 285 att atg ata tac aat gat ctc att aat ccc tat gct aat gat tct aac        912
Ile Met Ile Tyr Asn Asp Leu Ile Asn Pro Tyr Ala Asn Asp Ser Asn
    290                 295                 300 tca tct gga tgc att gtt act gtg gag aca aaa cct ggc ccc gat ttc        960
Ser Ser Gly Cys Ile Val Thr Val Glu Thr Lys Pro Gly Pro Asp Phe
305                 310                 315                 320 aaa ttt cac ctc ttg aaa ccg cct ggg tct atg tta act cat ggg tca       1008
Lys Phe His Leu Leu Lys Pro Pro Gly Ser Met Leu Thr His Gly Ser
                325                 330                 335 att cca tcc gac ctt atc cca aaa tct tct tct ctt tgg att ggc aac       1056
Ile Pro Ser Asp Leu Ile Pro Lys Ser Ser Ser Leu Trp Ile Gly Asn
            340                 345                 350 cga cac tgg tct gat ata act gat ttt gtc atc aaa cct ttt gtt ttc       1104
Arg His Trp Ser Asp Ile Thr Asp Phe Val Ile Lys Pro Phe Val Phe
        355                 360                 365 cag gct aat cga cat ttt gac ttc aat caa gag act gca ggc tgg agc       1152
Gln Ala Asn Arg His Phe Asp Phe Asn Gln Glu Thr Ala Gly Trp Ser
    370                 375                 380 act ccc aga ttt aga ccc ata acc atc aca gtt tct gag aag gga gga       1200
Thr Pro Arg Phe Arg Pro Ile Thr Ile Thr Val Ser Glu Lys Gly Gly
385                 390                 395                 400 tca aaa ttg ggt att ggt gtt gca act gac tct att gtc cct ggc ata       1248
Ser Lys Leu Gly Ile Gly Val Ala Thr Asp Ser Ile Val Pro Gly Ile
                405                 410                 415 cca gac ggc tgg ccg gat acc acc att cca gaa aaa ctt acc cca gca       1296
Pro Asp Gly Trp Pro Asp Thr Thr Ile Pro Glu Lys Leu Thr Pro Ala
            420                 425                 430 ggt gac tat gca atc aca aat ggg gga aac aat gac atc acc act gct       1344
Gly Asp Tyr Ala Ile Thr Asn Gly Gly Asn Asn Asp Ile Thr Thr Ala
        435                 440                 445 gcg gac tat gat ggg gca agt ata atc aaa aac aat aca aat ttc aag       1392
Ala Asp Tyr Asp Gly Ala Ser Ile Ile Lys Asn Asn Thr Asn Phe Lys
```

| | | |
|---|---|---|
| ggt atg tat att tgt ggt gct ttg caa aga gct tgg ggt gac aag aaa<br>Gly Met Tyr Ile Cys Gly Ala Leu Gln Arg Ala Trp Gly Asp Lys Lys<br>465                          470                        475                    480 | 1440 |
| att tca aac act gcc ttt atc act acc gca atc aga gag ggt aac tca<br>Ile Ser Asn Thr Ala Phe Ile Thr Thr Ala Ile Arg Glu Gly Asn Ser<br>                        485                        490                    495 | 1488 |
| ata aaa cca tct aat gta att gac atg aca aaa ctt gcc gtt tat caa<br>Ile Lys Pro Ser Asn Val Ile Asp Met Thr Lys Leu Ala Val Tyr Gln<br>500                          505                        510 | 1536 |
| gat gct cat gtt ggt gca gaa ctt caa acc tct gac atc acc tta gca<br>Asp Ala His Val Gly Ala Glu Leu Gln Thr Ser Asp Ile Thr Leu Ala<br>            515                      520                    525 | 1584 |
| atc ctt ggt tat acc ggg att ggt gaa gaa gct ata ggc ctg gat agg<br>Ile Leu Gly Tyr Thr Gly Ile Gly Glu Glu Ala Ile Gly Leu Asp Arg<br>530                          535                        540 | 1632 |
| gac aaa gtg gtg cgt att agc ata ctt cca gaa act ggt gct cgt ggc<br>Asp Lys Val Val Arg Ile Ser Ile Leu Pro Glu Thr Gly Ala Arg Gly<br>545                          550                        555                    560 | 1680 |
| gga aat cac cct att ttc tat atg aac aaa att aaa tta ggt tat gtt<br>Gly Asn His Pro Ile Phe Tyr Met Asn Lys Ile Lys Leu Gly Tyr Val<br>                          565                        570                    575 | 1728 |
| att aga tca ata gat gtg gca aac tcc caa att tta cat aca tct agg<br>Ile Arg Ser Ile Asp Val Ala Asn Ser Gln Ile Leu His Thr Ser Arg<br>            580                      585                    590 | 1776 |
| caa tta tca ctc aat aat tat cta ctg gct cct gac tcc ttt gca gtt<br>Gln Leu Ser Leu Asn Asn Tyr Leu Leu Ala Pro Asp Ser Phe Ala Val<br>595                          600                        605 | 1824 |
| tac aga att att gat tct ggc ggc tct tgg ttt gat att ggt att gat<br>Tyr Arg Ile Ile Asp Ser Gly Gly Ser Trp Phe Asp Ile Gly Ile Asp<br>            610                      615                    620 | 1872 |
| agt gat ggt ttt tct ttt gtt ggt gta tct caa att gga aaa ttg gag<br>Ser Asp Gly Phe Ser Phe Val Gly Val Ser Gln Ile Gly Lys Leu Glu<br>625                          630                        635                    640 | 1920 |
| ttt cca cta act gcc tcc tac atg gga att caa ttg gca aag att cga<br>Phe Pro Leu Thr Ala Ser Tyr Met Gly Ile Gln Leu Ala Lys Ile Arg<br>            645                      650                    655 | 1968 |
| ctt gcc tca aac att agg agt gga atg gtt aaa ata tga<br>Leu Ala Ser Asn Ile Arg Ser Gly Met Val Lys Ile<br>            660                      665 | 2007 |

<210> SEQ ID NO 4
<211> LENGTH: 668
<212> TYPE: PRT
<213> ORGANISM: Feline calcivirus

<400> SEQUENCE: 4

Met Cys Ser Thr Cys Ala Asn Val Leu Lys Tyr Tyr Asp Trp Asp Pro
1                 5                    10                  15

His Phe Arg Leu Ile Ile Asn Pro Asn Lys Phe Leu Ser Val Gly Phe
                  20                    25                  30

Cys Asp Asn Pro Leu Met Cys Cys Tyr Pro Glu Leu Leu Pro Glu Phe
              35                    40                    45

Gly Thr Val Trp Asp Cys Asp Gln Ser Pro Leu Gln Ile Tyr Leu Glu
        50                    55                    60

Ser Ile Leu Gly Asp Asp Glu Trp Ala Ser Thr Tyr Glu Ala Val Asp
65                70                    75                  80

Pro Val Val Pro Pro Met His Trp Asp Ser Ala Gly Lys Ile Phe Gln
                  85                    90                  95

-continued

```
Pro His Pro Gly Val Leu Met His His Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Val Thr Thr Pro Glu Gln Gly Thr Leu Val Gly Gly Val Ile Ala
        130                 135                 140

Glu Pro Asn Ala Gln Met Ser Ala Val Ala Asp Val Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
                180                 185                 190

Leu Gly Pro Leu Leu Asn Pro Tyr Leu Thr His Leu Ala Lys Leu Tyr
        195                 200                 205

Val Ala Trp Ser Gly Ser Ile Glu Val Arg Phe Ser Ile Ser Gly Ser
    210                 215                 220

Gly Val Phe Gly Gly Lys Leu Ala Ala Ile Val Val Pro Pro Gly Ile
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Thr Ile Pro Asp Leu Arg
                260                 265                 270

Asn Ser Leu Tyr His Leu Met Ser Asp Thr Asp Thr Thr Ser Leu Val
        275                 280                 285

Ile Met Ile Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Ser Ser Ser Leu Trp Ile Gly Asn
        340                 345                 350

Arg His Trp Ser Asp Ile Thr Asp Phe Val Ile Lys Pro Phe Val Phe
    355                 360                 365

Gln Ala Asn Arg His Phe Asp Phe Asn Gln Glu Thr Ala Gly Trp Ser
    370                 375                 380

Thr Pro Arg Phe Arg Pro Ile Thr Ile Thr Val Ser Glu Lys Gly Gly
385                 390                 395                 400

Ser Lys Leu Gly Ile Gly Val Ala Thr Asp Ser Ile Val Pro Gly Ile
                405                 410                 415

Pro Asp Gly Trp Pro Asp Thr Thr Ile Pro Glu Lys Leu Thr Pro Ala
                420                 425                 430

Gly Asp Tyr Ala Ile Thr Asn Gly Gly Asn Asn Asp Ile Thr Thr Ala
        435                 440                 445

Ala Asp Tyr Asp Gly Ala Ser Ile Ile Lys Asn Asn Thr Asn Phe Lys
    450                 455                 460

Gly Met Tyr Ile Cys Gly Ala Leu Gln Arg Ala Trp Gly Asp Lys Lys
465                 470                 475                 480

Ile Ser Asn Thr Ala Phe Ile Thr Thr Ala Ile Arg Glu Gly Asn Ser
                485                 490                 495

Ile Lys Pro Ser Asn Val Ile Asp Met Thr Lys Leu Ala Val Tyr Gln
        500                 505                 510
```

-continued

```
Asp Ala His Val Gly Ala Glu Leu Gln Thr Ser Asp Ile Thr Leu Ala
        515                 520                 525
Ile Leu Gly Tyr Thr Gly Ile Gly Glu Glu Ala Ile Gly Leu Asp Arg
    530                 535                 540
Asp Lys Val Val Arg Ile Ser Ile Leu Pro Glu Thr Gly Ala Arg Gly
545                 550                 555                 560
Gly Asn His Pro Ile Phe Tyr Met Asn Lys Ile Lys Leu Gly Tyr Val
                565                 570                 575
Ile Arg Ser Ile Asp Val Ala Asn Ser Gln Ile Leu His Thr Ser Arg
            580                 585                 590
Gln Leu Ser Leu Asn Asn Tyr Leu Leu Ala Pro Asp Ser Phe Ala Val
        595                 600                 605
Tyr Arg Ile Ile Asp Ser Gly Gly Ser Trp Phe Asp Ile Gly Ile Asp
    610                 615                 620
Ser Asp Gly Phe Ser Phe Val Gly Val Ser Gln Ile Gly Lys Leu Glu
625                 630                 635                 640
Phe Pro Leu Thr Ala Ser Tyr Met Gly Ile Gln Leu Ala Lys Ile Arg
                645                 650                 655
Leu Ala Ser Asn Ile Arg Ser Gly Met Val Lys Ile
            660                 665
```

<210> SEQ ID NO 5
<211> LENGTH: 3701
<212> TYPE: DNA
<213> ORGANISM: canarypox virus
<220> FEATURE:
<221> NAME/KEY: CDS
<222> LOCATION: (377)..(2254)
<223> OTHER INFORMATION: coding sequence of c6L

<400> SEQUENCE: 5

| | |
|---|---|
| aagcttctat caaaagtctt aatgagttag gtgtagatag tatagatatt actacaaagg | 60 |
| tattcatatt tcctatcaat tctaaagtag atgatattaa taactcaaag atgatgatag | 120 |
| tagataatag atacgctcat ataatgactg caaatttgga cggttcacat tttaatcatc | 180 |
| acgcgttcat aagtttcaac tgcatagatc aaaatctcac taaaaagata gccgatgtat | 240 |
| ttgagagaga ttggacatct aactacgcta agaaattac agttataaat aatacataat | 300 |
| ggatttttgtt atcatcagtt atatttaaca taagtacaat aaaaagtatt aaataaaaat | 360 |

```
acttacttac gaaaaa atg tca tta tta caa aaa cta tat ttt aca gaa caa      412
              Met Ser Leu Leu Gln Lys Leu Tyr Phe Thr Glu Gln
                1               5                   10 tct ata gta gag tcc ttt aag agt tat aat tta aaa gat aac cat aat         460
Ser Ile Val Glu Ser Phe Lys Ser Tyr Asn Leu Lys Asp Asn His Asn
    15                  20                  25 gta ata ttt acc aca tca gat gat gat act gtt gta gta ata aat gaa         508
Val Ile Phe Thr Thr Ser Asp Asp Asp Thr Val Val Val Ile Asn Glu
    30                  35                  40 gat aat gta ctg tta tct aca aga tta tta tca ttt gat aaa att ctg         556
Asp Asn Val Leu Leu Ser Thr Arg Leu Leu Ser Phe Asp Lys Ile Leu
45                  50                  55                  60 ttt ttt aac tcc ttt aat aac ggt tta tca aaa tac gaa act att agt         604
Phe Phe Asn Ser Phe Asn Asn Gly Leu Ser Lys Tyr Glu Thr Ile Ser
                65                  70                  75 gat aca ata tta gat ata gat act cat aat tat tat ata cct agt tct         652
Asp Thr Ile Leu Asp Ile Asp Thr His Asn Tyr Tyr Ile Pro Ser Ser
            80                  85                  90 tct tct ttg tta gat att cta aaa aaa aga gcg tgt gat tta gaa tta         700
```

```
                                                    -continued

Ser Ser Leu Leu Asp Ile Leu Lys Lys Arg Ala Cys Asp Leu Glu Leu
        95              100                 105 gaa gat cta aat tat gcg tta ata gga gac aat agt aac tta tat tat      748
Glu Asp Leu Asn Tyr Ala Leu Ile Gly Asp Asn Ser Asn Leu Tyr Tyr
    110             115                 120 aaa gat atg act tac atg aat aat tgg tta ttt act aaa gga tta tta      796
Lys Asp Met Thr Tyr Met Asn Asn Trp Leu Phe Thr Lys Gly Leu Leu
125             130                 135                 140 gat tac aag ttt gta tta ttg cgc gat gta gat aaa tgt tac aaa cag      844
Asp Tyr Lys Phe Val Leu Leu Arg Asp Val Asp Lys Cys Tyr Lys Gln
                145                 150                 155 tat aat aaa aag aat act ata ata gat ata ata cat cgc gat aac aga      892
Tyr Asn Lys Lys Asn Thr Ile Ile Asp Ile Ile His Arg Asp Asn Arg
            160                 165                 170 cag tat aac ata tgg gtt aaa aat gtt ata gaa tac tgt tct cct ggc      940
Gln Tyr Asn Ile Trp Val Lys Asn Val Ile Glu Tyr Cys Ser Pro Gly
        175                 180                 185 tat ata tta tgg tta cat gat cta aaa gcc gct gct gaa gat gat tgg      988
Tyr Ile Leu Trp Leu His Asp Leu Lys Ala Ala Ala Glu Asp Asp Trp
    190                 195                 200 tta aga tac gat aac cgt ata aac gaa tta tct gcg gat aaa tta tac     1036
Leu Arg Tyr Asp Asn Arg Ile Asn Glu Leu Ser Ala Asp Lys Leu Tyr
205                 210                 215                 220 act ttc gag ttc ata gtt ata tta gaa aat aat ata aaa cat tta cga     1084
Thr Phe Glu Phe Ile Val Ile Leu Glu Asn Asn Ile Lys His Leu Arg
                225                 230                 235 gta ggt aca ata att gta cat cca aac aag ata ata gct aat ggt aca     1132
Val Gly Thr Ile Ile Val His Pro Asn Lys Ile Ile Ala Asn Gly Thr
            240                 245                 250 tct aat aat ata ctt act gat ttt cta tct tac gta gaa gaa cta ata     1180
Ser Asn Asn Ile Leu Thr Asp Phe Leu Ser Tyr Val Glu Glu Leu Ile
        255                 260                 265 tat cat cat aat tca tct ata ata ttg gcc gga tat ttt tta gaa ttc     1228
Tyr His His Asn Ser Ser Ile Ile Leu Ala Gly Tyr Phe Leu Glu Phe
    270                 275                 280 ttt gag acc act att tta tca gaa ttt att tct tca tct tct gaa tgg     1276
Phe Glu Thr Thr Ile Leu Ser Glu Phe Ile Ser Ser Ser Ser Glu Trp
285                 290                 295                 300 gta atg aat agt aac tgt tta gta cac ctg aaa aca ggg tat gaa gct     1324
Val Met Asn Ser Asn Cys Leu Val His Leu Lys Thr Gly Tyr Glu Ala
                305                 310                 315 ata ctc ttt gat gct agt tta ttt ttc caa ctc tct act aaa agc aat     1372
Ile Leu Phe Asp Ala Ser Leu Phe Phe Gln Leu Ser Thr Lys Ser Asn
            320                 325                 330 tat gta aaa tat tgg aca aag aaa act ttg cag tat aag aac ttt ttt     1420
Tyr Val Lys Tyr Trp Thr Lys Lys Thr Leu Gln Tyr Lys Asn Phe Phe
        335                 340                 345 aaa gac ggt aaa cag tta gca aaa tat ata att aag aaa gat agt cag     1468
Lys Asp Gly Lys Gln Leu Ala Lys Tyr Ile Ile Lys Lys Asp Ser Gln
    350                 355                 360 gtg ata gat aga gta tgt tat tta cac gca gct gta tat aat cac gta     1516
Val Ile Asp Arg Val Cys Tyr Leu His Ala Ala Val Tyr Asn His Val
365                 370                 375                 380 act tac tta atg gat acg ttt aaa att cct ggt ttt gat ttt aaa ttc     1564
Thr Tyr Leu Met Asp Thr Phe Lys Ile Pro Gly Phe Asp Phe Lys Phe
                385                 390                 395 tcc gga atg ata gat ata cta ctg ttt gga ata ttg cat aag gat aat     1612
Ser Gly Met Ile Asp Ile Leu Leu Phe Gly Ile Leu His Lys Asp Asn
            400                 405                 410
```

```
                                                    -continued gag aat ata ttt tat ccg aaa cgt gtt tct gta act aat ata ata tca    1660
Glu Asn Ile Phe Tyr Pro Lys Arg Val Ser Val Thr Asn Ile Ile Ser
            415                 420                 425 gaa tct atc tat gca gat ttt tac ttt ata tca gat gtt aat aaa ttc    1708
Glu Ser Ile Tyr Ala Asp Phe Tyr Phe Ile Ser Asp Val Asn Lys Phe
430                 435                 440 agt aaa aag ata gaa tat aaa act atg ttt cct ata ctc gca gaa aac    1756
Ser Lys Lys Ile Glu Tyr Lys Thr Met Phe Pro Ile Leu Ala Glu Asn
445                 450                 455                 460 tac tat cca aaa gga agg ccc tat ttt aca cat aca tct aac gaa gat    1804
Tyr Tyr Pro Lys Gly Arg Pro Tyr Phe Thr His Thr Ser Asn Glu Asp
                465                 470                 475 ctt ctg tct atc tgt tta tgc gaa gta aca gtt tgt aaa gat ata aaa    1852
Leu Leu Ser Ile Cys Leu Cys Glu Val Thr Val Cys Lys Asp Ile Lys
            480                 485                 490 aat cca tta tta tat tct aaa aag gat ata tca gca aaa cga ttc ata    1900
Asn Pro Leu Leu Tyr Ser Lys Lys Asp Ile Ser Ala Lys Arg Phe Ile
        495                 500                 505 ggt tta ttt aca tct gtc gat ata aat acg gct gtt gag tta aga gga    1948
Gly Leu Phe Thr Ser Val Asp Ile Asn Thr Ala Val Glu Leu Arg Gly
510                 515                 520 tat aaa ata aga gta ata gga tgt tta gaa tgg cct gaa aag ata aaa    1996
Tyr Lys Ile Arg Val Ile Gly Cys Leu Glu Trp Pro Glu Lys Ile Lys
525                 530                 535                 540 ata ttt aat tct aat cct aca tac att aga tta tta cta aca gaa aga    2044
Ile Phe Asn Ser Asn Pro Thr Tyr Ile Arg Leu Leu Leu Thr Glu Arg
                545                 550                 555 cgt tta gat att cta cat tcc tat ctg ctt aaa ttt aat ata aca gag    2092
Arg Leu Asp Ile Leu His Ser Tyr Leu Leu Lys Phe Asn Ile Thr Glu
            560                 565                 570 gat ata gct acc aga gat gga gtc aga aat aat tta cct ata att tct    2140
Asp Ile Ala Thr Arg Asp Gly Val Arg Asn Asn Leu Pro Ile Ile Ser
        575                 580                 585 ttt atc gtc agt tat tgt aga tcg tat act tat aaa tta cta aat tgc    2188
Phe Ile Val Ser Tyr Cys Arg Ser Tyr Thr Tyr Lys Leu Leu Asn Cys
590                 595                 600 cat atg tac aat tcg tgt aag ata aca aag tgt aaa tat aat cag gta    2236
His Met Tyr Asn Ser Cys Lys Ile Thr Lys Cys Lys Tyr Asn Gln Val
605                 610                 615                 620 ata tat aat cct ata tag gagtatatat aattgaaaaa gtaaaatata            2284
Ile Tyr Asn Pro Ile
                625 aatcatataa taatgaaacg aaatatcagt aatagacagg aactggcaga ttcttcttct   2344 aatgaagtaa gtactgctaa atctccaaaa ttagataaaa atgatacagc aaatacagct   2404 tcattcaacg aattacctttt taattttttc agacacacct tattcaaaac taactaagtc  2464 agatgatgag aaagtaaata taaatttaac ttatgggtat aatataataa agattcatga   2524 tattaataat ttacttaacg atgttaatag acttattcca tcaacccctt caaacctttc   2584 tggatattat aaaataccag ttaatgatat taaaatagat tgtttaagag atgtaaataa   2644 ttatttggag gtaaaggata taaaattagt ctatctttca catggaaatg aattacctaa   2704 tattaataat tatgatagga attttttagg atttacagct gttatatgta tcaacaatac   2764 aggcagatct atggttatgg taaaacactg taacgggaag cagcattcta tggtaactgg   2824 cctatgttta atagccagat catttttactc tataaacatt ttaccacaaa taataggatc  2884 ctctagatat ttaatattat atctaacaac aacaaaaaaa tttaacgatg tatggccaga   2944 agtattttct actaataaag ataaagatag tctatcttat ctacaagata tgaaagaaga   3004
```

-continued

```
taatcattta gtagtagcta ctaatatgga aagaaatgta tacaaaaacg tggaagcttt     3064
tatattaaat agcatattac tagaagattt aaaatctaga cttagtataa caaaacagtt     3124
aaatgccaat atcgattcta tatttcatca taacagtagt acattaatca gtgatatact     3184
gaaacgatct acagactcaa ctatgcaagg aataagcaat atgccaatta tgtctaatat     3244 tttaactttta gaactaaaac gttctaccaa tactaaaaat aggatacgtg ataggctgtt     3304
aaaagctgca ataaatagta aggatgtaga agaaatactt tgttctatac cttcggagga     3364 aagaactttta gaacaactta agtttaatca aacttgtatt tatgaacact ataaaaaaat     3424
tatggaagat acaagtaaaa gaatggatgt tgaatgtcgt agtttagaac ataactatac     3484
ggctaactta tataaagtgt acggacaaaa cgaatatatg attacttata tactagctct     3544
cataagtagg attaataata ttatagaaac tttaaaatat aatctggtgg ggctagacga     3604
atctacaata cgtaatataa attatataat ttcacaaaga acaaaaaaaa atcaagtttc     3664 taataccttta tagataaact atattttta ccactga                              3701
```

<210> SEQ ID NO 6
<211> LENGTH: 625
<212> TYPE: PRT
<213> ORGANISM: canarypox virus

<400> SEQUENCE: 6

```
Met Ser Leu Leu Gln Lys Leu Tyr Phe Thr Glu Gln Ser Ile Val Glu
1               5                   10                  15

Ser Phe Lys Ser Tyr Asn Leu Lys Asp Asn His Asn Val Ile Phe Thr
            20                  25                  30

Thr Ser Asp Asp Thr Val Val Ile Asn Glu Asp Asn Val Leu
        35                  40                  45

Leu Ser Thr Arg Leu Leu Ser Phe Asp Lys Ile Leu Phe Phe Asn Ser
    50                  55                  60

Phe Asn Asn Gly Leu Ser Lys Tyr Glu Thr Ile Ser Asp Thr Ile Leu
65                  70                  75                  80

Asp Ile Asp Thr His Asn Tyr Tyr Ile Pro Ser Ser Ser Leu Leu
                85                  90                  95

Asp Ile Leu Lys Lys Arg Ala Cys Asp Leu Glu Leu Glu Asp Leu Asn
            100                 105                 110

Tyr Ala Leu Ile Gly Asp Asn Ser Asn Leu Tyr Tyr Lys Asp Met Thr
        115                 120                 125

Tyr Met Asn Asn Trp Leu Phe Thr Lys Gly Leu Leu Asp Tyr Lys Phe
    130                 135                 140

Val Leu Leu Arg Asp Val Asp Lys Cys Tyr Lys Gln Tyr Asn Lys Lys
145                 150                 155                 160

Asn Thr Ile Ile Asp Ile Ile His Arg Asp Asn Arg Gln Tyr Asn Ile
                165                 170                 175

Trp Val Lys Asn Val Ile Glu Tyr Cys Ser Pro Gly Tyr Ile Leu Trp
            180                 185                 190

Leu His Asp Leu Lys Ala Ala Glu Asp Asp Trp Leu Arg Tyr Asp
        195                 200                 205

Asn Arg Ile Asn Glu Leu Ser Ala Asp Lys Leu Tyr Thr Phe Glu Phe
    210                 215                 220

Ile Val Ile Leu Glu Asn Asn Ile Lys His Leu Arg Val Gly Thr Ile
225                 230                 235                 240

Ile Val His Pro Asn Lys Ile Ile Ala Asn Gly Thr Ser Asn Asn Ile
```

245                 250                 255
Leu Thr Asp Phe Leu Ser Tyr Val Glu Glu Leu Ile Tyr His His Asn
                260                 265                 270
Ser Ser Ile Ile Leu Ala Gly Tyr Phe Leu Glu Phe Glu Thr Thr
            275                 280                 285
Ile Leu Ser Glu Phe Ile Ser Ser Ser Glu Trp Val Met Asn Ser
    290                 295                 300
Asn Cys Leu Val His Leu Lys Thr Gly Tyr Glu Ala Ile Leu Phe Asp
305                 310                 315                 320
Ala Ser Leu Phe Phe Gln Leu Ser Thr Lys Ser Asn Tyr Val Lys Tyr
                325                 330                 335
Trp Thr Lys Lys Thr Leu Gln Tyr Lys Asn Phe Phe Lys Asp Gly Lys
                340                 345                 350
Gln Leu Ala Lys Tyr Ile Ile Lys Lys Asp Ser Gln Val Ile Asp Arg
            355                 360                 365
Val Cys Tyr Leu His Ala Ala Val Tyr Asn His Val Thr Tyr Leu Met
    370                 375                 380
Asp Thr Phe Lys Ile Pro Gly Phe Asp Phe Lys Phe Ser Gly Met Ile
385                 390                 395                 400
Asp Ile Leu Leu Phe Gly Ile Leu His Lys Asp Asn Glu Asn Ile Phe
                405                 410                 415
Tyr Pro Lys Arg Val Ser Val Thr Asn Ile Ile Ser Glu Ser Ile Tyr
                420                 425                 430
Ala Asp Phe Tyr Phe Ile Ser Asp Val Asn Lys Phe Ser Lys Lys Ile
            435                 440                 445
Glu Tyr Lys Thr Met Phe Pro Ile Leu Ala Glu Asn Tyr Tyr Pro Lys
    450                 455                 460
Gly Arg Pro Tyr Phe Thr His Thr Ser Asn Glu Asp Leu Leu Ser Ile
465                 470                 475                 480
Cys Leu Cys Glu Val Thr Val Cys Lys Asp Ile Lys Asn Pro Leu Leu
                485                 490                 495
Tyr Ser Lys Lys Asp Ile Ser Ala Lys Arg Phe Ile Gly Leu Phe Thr
                500                 505                 510
Ser Val Asp Ile Asn Thr Ala Val Glu Leu Arg Gly Tyr Lys Ile Arg
            515                 520                 525
Val Ile Gly Cys Leu Glu Trp Pro Glu Lys Ile Lys Ile Phe Asn Ser
    530                 535                 540
Asn Pro Thr Tyr Ile Arg Leu Leu Leu Thr Glu Arg Arg Leu Asp Ile
545                 550                 555                 560
Leu His Ser Tyr Leu Leu Lys Phe Asn Ile Thr Glu Asp Ile Ala Thr
                565                 570                 575
Arg Asp Gly Val Arg Asn Asn Leu Pro Ile Ile Ser Phe Ile Val Ser
            580                 585                 590
Tyr Cys Arg Ser Tyr Thr Tyr Lys Leu Leu Asn Cys His Met Tyr Asn
    595                 600                 605
Ser Cys Lys Ile Thr Lys Cys Lys Tyr Asn Gln Val Ile Tyr Asn Pro
    610                 615                 620
Ile
625

<210> SEQ ID NO 7
<211> LENGTH: 432
<212> TYPE: DNA
<213> ORGANISM: Felis sp.

<220> FEATURE:
<221> NAME/KEY: CDS
<222> LOCATION: (1)..(429)
<223> OTHER INFORMATION: coding sequence of 3R3 feline GM-CSF gene
<220> FEATURE:
<221> NAME/KEY: variation
<222> LOCATION: (319)..(319)
<223> OTHER INFORMATION: A change of 'c' to 't' at the nucleotide level
      causes a change of leucine to phenylalanine for the amino aci

<400> SEQUENCE: 7

```
atg tgg ctg cag aac ctg ctt ttc ctg ggc act gtg gtc tgc agc atc        48
Met Trp Leu Gln Asn Leu Leu Phe Leu Gly Thr Val Val Cys Ser Ile
1               5                   10                  15 tct gca ccc acc agt tca ccc agc tct gtc act cgg ccc tgg caa cac        96
Ser Ala Pro Thr Ser Ser Pro Ser Ser Val Thr Arg Pro Trp Gln His
            20                  25                  30 gtg gat gcc atc aag gag gct ctg agc ctt ctg aac aac agt agt gaa       144
Val Asp Ala Ile Lys Glu Ala Leu Ser Leu Leu Asn Asn Ser Ser Glu
        35                  40                  45 ata act gct gtg atg aat gaa gca gta gaa gtc gtc tct gaa atg ttt       192
Ile Thr Ala Val Met Asn Glu Ala Val Glu Val Val Ser Glu Met Phe
    50                  55                  60 gac cct gag gag ccg aaa tgc ctg cag act cac cta aag ctg tac gag       240
Asp Pro Glu Glu Pro Lys Cys Leu Gln Thr His Leu Lys Leu Tyr Glu
65                  70                  75                  80 cag ggc cta cgg ggc agc ctc atc agc ctc aag gag cct ctg aga atg       288
Gln Gly Leu Arg Gly Ser Leu Ile Ser Leu Lys Glu Pro Leu Arg Met
                85                  90                  95 atg gcc aac cat tac aag cag cac tgc ccc ttt act ccg gaa acg ccc       336
Met Ala Asn His Tyr Lys Gln His Cys Pro Phe Thr Pro Glu Thr Pro
            100                 105                 110 tgt gaa acc cag act atc acc ttc aaa aat ttc aaa gag aat ctg aag       384
Cys Glu Thr Gln Thr Ile Thr Phe Lys Asn Phe Lys Glu Asn Leu Lys
        115                 120                 125 gat ttt ctg ttt aac atc ccc ttt gac tgc tgg aaa cca gtc aag aag       432
Asp Phe Leu Phe Asn Ile Pro Phe Asp Cys Trp Lys Pro Val Lys Lys
    130                 135                 140
```

<210> SEQ ID NO 8
<211> LENGTH: 143
<212> TYPE: PRT
<213> ORGANISM: Felis sp.

<400> SEQUENCE: 8

```
Met Trp Leu Gln Asn Leu Leu Phe Leu Gly Thr Val Val Cys Ser Ile
1               5                   10                  15

Ser Ala Pro Thr Ser Ser Pro Ser Ser Val Thr Arg Pro Trp Gln His
            20                  25                  30

Val Asp Ala Ile Lys Glu Ala Leu Ser Leu Leu Asn Asn Ser Ser Glu
        35                  40                  45

Ile Thr Ala Val Met Asn Glu Ala Val Glu Val Val Ser Glu Met Phe
    50                  55                  60

Asp Pro Glu Glu Pro Lys Cys Leu Gln Thr His Leu Lys Leu Tyr Glu
65                  70                  75                  80

Gln Gly Leu Arg Gly Ser Leu Ile Ser Leu Lys Glu Pro Leu Arg Met
                85                  90                  95

Met Ala Asn His Tyr Lys Gln His Cys Pro Phe Thr Pro Glu Thr Pro
            100                 105                 110

Cys Glu Thr Gln Thr Ile Thr Phe Lys Asn Phe Lys Glu Asn Leu Lys
        115                 120                 125
```

```
Asp Phe Leu Phe Asn Ile Pro Phe Asp Cys Trp Lys Pro Val Lys
    130                 135                 140
```

```
<210> SEQ ID NO 9
<211> LENGTH: 432
<212> TYPE: DNA
<213> ORGANISM: Felis sp.
<220> FEATURE:
<221> NAME/KEY: CDS
<222> LOCATION: (1)..(429)
<223> OTHER INFORMATION: coding sequence of 3R4 feline GM-CSF gene

<400> SEQUENCE: 9 atg tgg ctg cag aac ctg ctt ttc ctg ggc act gtg gtc tgc agc atc        48
Met Trp Leu Gln Asn Leu Leu Phe Leu Gly Thr Val Val Cys Ser Ile
1               5                   10                  15 tct gca ccc acc agt tca ccc agc tct gtc act cgg ccc tgg caa cac        96
Ser Ala Pro Thr Ser Ser Pro Ser Ser Val Thr Arg Pro Trp Gln His
            20                  25                  30 gtg gat gcc atc aag gag gct ctg agc ctt ctg aac aac agt agt gaa       144
Val Asp Ala Ile Lys Glu Ala Leu Ser Leu Leu Asn Asn Ser Ser Glu
        35                  40                  45 ata act gct gtg atg aat gaa gca gta gaa gtc gtc tct gaa atg ttt       192
Ile Thr Ala Val Met Asn Glu Ala Val Glu Val Val Ser Glu Met Phe
    50                  55                  60 gac cct gag gag ccg aaa tgc ctg cag act cac cta aag ctg tac gag       240
Asp Pro Glu Glu Pro Lys Cys Leu Gln Thr His Leu Lys Leu Tyr Glu
65                  70                  75                  80 cag ggc cta cgg ggc agc ctc atc agc ctc aag gag cct ctg agg atg       288
Gln Gly Leu Arg Gly Ser Leu Ile Ser Leu Lys Glu Pro Leu Arg Met
                85                  90                  95 atg gcc aac cat tac aag cag cac tgc ccc ctt act ccg gaa acg ccc       336
Met Ala Asn His Tyr Lys Gln His Cys Pro Leu Thr Pro Glu Thr Pro
            100                 105                 110 tgt gaa acc cag act atc acc ttc aaa aat ttc aaa gag aat ctg aag       384
Cys Glu Thr Gln Thr Ile Thr Phe Lys Asn Phe Lys Glu Asn Leu Lys
        115                 120                 125 gat ttt ctg ttt aac atc ccc ttt gac tgc tgg aaa cca gtc aag aag       432
Asp Phe Leu Phe Asn Ile Pro Phe Asp Cys Trp Lys Pro Val Lys Lys
    130                 135                 140
```

```
<210> SEQ ID NO 10
<211> LENGTH: 143
<212> TYPE: PRT
<213> ORGANISM: Felis sp.

<400> SEQUENCE: 10

Met Trp Leu Gln Asn Leu Leu Phe Leu Gly Thr Val Val Cys Ser Ile
1               5                   10                  15

Ser Ala Pro Thr Ser Ser Pro Ser Ser Val Thr Arg Pro Trp Gln His
            20                  25                  30

Val Asp Ala Ile Lys Glu Ala Leu Ser Leu Leu Asn Asn Ser Ser Glu
        35                  40                  45

Ile Thr Ala Val Met Asn Glu Ala Val Glu Val Val Ser Glu Met Phe
    50                  55                  60

Asp Pro Glu Glu Pro Lys Cys Leu Gln Thr His Leu Lys Leu Tyr Glu
65                  70                  75                  80

Gln Gly Leu Arg Gly Ser Leu Ile Ser Leu Lys Glu Pro Leu Arg Met
                85                  90                  95
```

```
Met Ala Asn His Tyr Lys Gln His Cys Pro Leu Thr Pro Glu Thr Pro
            100                 105                 110

Cys Glu Thr Gln Thr Ile Thr Phe Lys Asn Phe Lys Glu Asn Leu Lys
        115                 120                 125

Asp Phe Leu Phe Asn Ile Pro Phe Asp Cys Trp Lys Pro Val Lys
    130                 135                 140

<210> SEQ ID NO 11
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer PB331

<400> SEQUENCE: 11
ttgcggccgc tgtgatgtgt tcgaagtttg agc                              33

<210> SEQ ID NO 12
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer PB333

<400> SEQUENCE: 12
ttggcgccgy tgaccmagtg cagcyttrtc caattc                           36

<210> SEQ ID NO 13
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: primer PB332

<400> SEQUENCE: 13
ttggcgccaa ywgtrttwgh tacagtrtca atyarrcc                         38

<210> SEQ ID NO 14
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer JCA289

<400> SEQUENCE: 14
aaacgcgtcg acatgtgctc aacctgcgct aacgtg                           36

<210> SEQ ID NO 15
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer JCA290

<400> SEQUENCE: 15
ttttgatatc tcatatttta accattccac tcc                              33
```

```
<210> SEQ ID NO 16
<211> LENGTH: 42
<212> TYPE: DNA
<213> ORGANISM: Artificial Sequence
<220> FEATURE:
<221> NAME/KEY: misc_feature
<222> LOCATION: (1)..(42)
<223> OTHER INFORMATION: primer C6A1

<400> SEQUENCE: 16
atcatcgagc tcgcggccgc ctatcaaaag tcttaatgag tt                    42

<210> SEQ ID NO 17
<211> LENGTH: 73
<212> TYPE: DNA
<213> ORGANISM: Artificial Sequence
<220> FEATURE:
<221> NAME/KEY: misc_feature
<222> LOCATION: (1)..(73)
<223> OTHER INFORMATION: primer C6B1

<400> SEQUENCE: 17
gaattcctcg agctgcagcc cgggttttta tagctaatta gtcatttttt cgtaagtaag    60 tattttttatt taa                                                     73

<210> SEQ ID NO 18
<211> LENGTH: 72
<212> TYPE: DNA
<213> ORGANISM: Artificial Sequence
<220> FEATURE:
<221> NAME/KEY: misc_feature
<222> LOCATION: (1)..(72)
<223> OTHER INFORMATION: primer C6C1

<400> SEQUENCE: 18
cccgggctgc agctcgagga attcttttta ttgattaact agtcaaatga gtatatataa    60
ttgaaaaagt aa                                                       72

<210> SEQ ID NO 19
<211> LENGTH: 45
<212> TYPE: DNA
<213> ORGANISM: Artificial Sequence
<220> FEATURE:
<221> NAME/KEY: misc_feature
<222> LOCATION: (1)..(45)
<223> OTHER INFORMATION: primer C6D1

<400> SEQUENCE: 19
gatgatggta ccttcataaa tacaagtttg attaaactta gttg                    45

<210> SEQ ID NO 20
<211> LENGTH: 34
<212> TYPE: DNA
<213> ORGANISM: Artificial Sequence
<220> FEATURE:
<221> NAME/KEY: misc_feature
<222> LOCATION: (1)..(34)
<223> OTHER INFORMATION: primer JCA291

<400> SEQUENCE: 20
aaacccgggt tctttattct atacttaaaa agtg                               34

<210> SEQ ID NO 21
<211> LENGTH: 43
<212> TYPE: DNA
<213> ORGANISM: Artificial Sequence
```

-continued

```
<220> FEATURE:
<221> NAME/KEY: misc_feature
<222> LOCATION: (1)..(43)
<223> OTHER INFORMATION: primer JCA292

<400> SEQUENCE: 21
aaaagaattc gtcgactacg atacaaactt aacggatatc gcg                    43

<210> SEQ ID NO 22
<211> LENGTH: 55
<212> TYPE: DNA
<213> ORGANISM: Artificial Sequence
<220> FEATURE:
<221> NAME/KEY: misc_feature
<222> LOCATION: (1)..(55)
<223> OTHER INFORMATION: primer JCA293

<400> SEQUENCE: 22
aaatcgcgat atccgttaag tttgtatcgt aatgtgctca acctgcgcta acgtg       55

<210> SEQ ID NO 23
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer JCA294

<400> SEQUENCE: 23
ttttgtcgac tcatatttta accattccac tcc                               33

<210> SEQ ID NO 24
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer JCA295

<400> SEQUENCE: 24
ttttgtcgac tcatagtttt gtcatagtac tcc                               33

<210> SEQ ID NO 25
<211> LENGTH: 33
<212> TYPE: DNA
<213> ORGANISM: Artificial Sequence
<220> FEATURE:
<221> NAME/KEY: misc_feature
<222> LOCATION: (1)..(33)
<223> OTHER INFORMATION: primer JP578

<400> SEQUENCE: 25
tatgcggccg ccaccatgtg gctgcagaac ctg                               33

<210> SEQ ID NO 26
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: primer JP579

<400> SEQUENCE: 26
tatgcggccg ctacgtatca cttcttgact ggtttc                            36
```

FELINE CALICIVIRUS GENES AND VACCINES IN PARTICULAR RECOMBINANT VACCINES

CROSS-REFERENCE TO RELATED APPLICATIONS

This application is a divisional of U.S. Ser. No. 09/617,594, filed Jul. 14, 2000, now U.S. Pat. No. 6,541,458, and claims priority from French application number 99 09421, filed Jul. 16, 1999, French application number 00 01761, filed Feb. 11, 2000, and U.S. Provisional application Ser. No. 60/193,332, filed Mar. 30, 2000. Each of the foregoing applications, patents and publications and all documents cited or referenced therein ("application cited documents") and all documents cited or referenced in this specification ("herein cited documents") and all documents referenced or cited in herein cited documents and in application cited documents, including during the prosecution of any of the applications, patents and application cited documents, are hereby incorporated by reference.

The present invention relates to genes of particular strains of feline caliciviruses, to the proteins encoded by these genes, and their use for the production of immunogenic preparations and of recombinant or subunit vaccines against feline calicivirosis. These immunogenic preparations and these vaccines may also be combined with immunogenic preparations or vaccines prepared on the basis of other feline pathogens, for the production of multivalent immunogenic preparations and vaccines.

BACKGROUND OF THE INVENTION

Feline caliciviruses (FCV) were first described in 1957 (Fastier L. B. Am. J. Vet. Res. 1957. 18, 382–389). Feline caliciviruses are, with the feline herpesviruses, the two principal sources of viral diseases of the upper respiratory tract in cats. The FCV viruses affect a large number of animals, with FCV carrying rates of the order of 15 to 25%, and an anti-FCV seroprevalence of 70 to 100% (Coutts et al. Vet. Rec. 1994. 135. 555–556; Ellis T. M. Australian Vet. J. 1981. 57. 115–118; Harbour et al. Vet. Rec. 1991. 128. 77–80; Reubel et al. Feline Dendistry 1992. 22. 1347–1360). After an initial phase of hyperthermia, these respiratory diseases are generally accompanied by buccal ulcerations (palate, tongue, lips, nose), rhinitis, conjunctivitis, possibly anorexia and asthenia. The FCV viruses can also cause pneumonia, enteritis, and articular pain (lameness syndrome).

The FCV virus is transmitted only horizontally, there is no vertical transmission from the mother to its kitten during gestation (Johnson R. P. Res. Vet. Sci. 1984. 31. 114–119). FCV is transmitted by contact between infected animals and healthy animals or by the airways during sneezing (Wardley RC. Arch. Virol. 1976. 52. 243–249).

Feline caliciviruses are naked viruses of the Caliciviridae family; they possess a single-stranded positive RNA of about 7.7 kilobase pairs (kbp) in size (Carter M. J. Arch. Virol. 1994. 9. 429–439).

Like many RNA viruses, a large heterogeneity exists within the viral population of FCV. The antigenic variations, demonstrated since the beginning of the 70s by cross-serum neutralization experiments, make it possible to classify the FCVs into several viral strains or quasispecies (Radfoord et al. Proc. 1$^{st}$ Int. Symp. Caliciviruses ESVV 1997. 93–99).

Several FCV strains have been isolated and sequenced, in particular the strain F9 (Carter et al. Arch. Virol. 1992. 122. 223–235, sequence deposited in the GenBank databank under the accession number M86379), FCI (Neill et al. J. Virol. 1991. 65. 5440–5447, GenBank accession number U13992 and M32819), Urbana or URB (Sosnovtsev and Green Virology 1995. 210. 383–390, GenBank accession number L40021), F4 (Tohya et al. Arch. Virol. 1991. 117. 173–181, GenBank accession numbers D31836 and D90357), KCD (Fastier L. B. Am. J. Vet. Res. 1957. 18. 882–889, GenBank accession number L09719), LLK (GenBank accession number U07131), NADC (GenBank accession number L09718), 2280 (GenBank accession number X99445) and 255 (Kahn and Gillepsie. Cornell Vet. 1970. 60. 669–683, GenBank accession number U07130).

Vaccination against FCV was introduced since the end of the 70s from attenuated FCV strains, mainly strain F9 isolated in 1958 by Bittle (Bittle et al. Am. J. Vet. Res. 1960. 21. 547–550) or strains derived from F9 by passage in vitro or in vivo ("F9-like").

Inactivated vaccines are also available. They use strains 255 and 2280, which were isolated respectively in 1970 in a cat with a pneumonia (Kahn and Gillepsie. Cornell Vet. 1970. 60. 669–683) and in 1983 in a cat suffering from lameness (Pedersen et al. Fel. Prac. 1983. 13. 26–35).

The humoral response is essentially directed against the capsid protein, also called p65 (Guiver et al. J. Gen. Virol. 1992. 73. 2429–2433). The genes encoding the capsid protein of many feline caliciviruses have been sequenced and compared without it being possible to distinguish more clearly certain sequences (Glenn et al. Proc. 1$_{st}$ Int. Symp. Caliciviruses ESVV 1997. 106–110; Geissler et al. Virus Res. 1997. 48. 193–206; Neill et al. Proc. 1$^{st}$ Int. Symp. Caliciviruses ESVV 1997. 120–124).

The gene encoding the capsid protein has also been cloned and expressed in various expression systems, in particular the gene encoding the capsid protein of the KS20 FCV virus in plasmids (Geissler et al. J. Virol. 1999. 73. 834–838), the genes encoding the capsid proteins of the CFI-68, JOK63, JOK92, LS012 and F9 FCV viruses in baculoviruses (DeSilver et al. Proc. 1$^{st}$ Int. Symp. Caliciviruses ESVV 1997. 131–143), the gene encoding the capsid protein of the F4 FCV virus in type 1 feline herpesviruses (Yokoyama et al. J. Vet. Med. Sci. 1998. 60. 717–723). These various constructs have allowed the production of recombinant capsid proteins.

Because of antigenic drift over time, antisera produced against old vaccine strains isolated in the 60–70s, such as strains F9, 255 or 2280, neutralize only few isolates of the 90s. For example, the anti-F9 serum neutralizes 43% of the isolates of the period 1990–1996, against 56% for the period 1980–89 and 86% for the period 1958–79, and only 10% of the English isolates of the period 1990–96 (Lauritzen et al. Vet. Microbiol. 1997. 56. 55–63).

The objective of the present invention is the detection of FCV strains, which induce in cats antibodies against a broad cross-neutralization spectrum.

BRIEF SUMMARY OF THE INVENTION

The objective of the invention is in particular, starting with selected strains, the isolation and characterization of genes encoding immunogenic proteins which can be used for vaccination against feline calicivirosis.

Another objective of the invention is to provide recombinant in vitro and in vivo expression vectors containing and expressing at least one such nucleotide sequence.

Yet another objective of the invention is to provide immunogenic preparations or vaccines against feline calicivirosis.

Yet another objective of the invention is to provide multivalent immunogenic preparations and multivalent vaccines against feline calicivirosis and against at least one other feline pathogen.

BRIEF DESCRIPTION OF THE FIGURES

FIG. 1: Nucleotide and amino acid sequence (SEQ ID NOs: 1 and 2) of the "capsid" protein of FCV G1 strain.

FIG. 2: Nucleotide and amino acid sequence (SEQ ID NOs: 3 and 4) of the "capsid" protein of FCV 431 strain.

FIG. 4: Nucleotide and amino acid sequence of the c6L region of the genome (SEQ ID NOs: 5 and 6) of the canarypox virus (strain ALVAC).

FIG. 6: Nucleotide and amino acid sequence of the 3R3 feline GM-CSF gene (SEQ ID NOs: 7and8).

FIG. 8: Nucleotide and amino acid sequence of the 3R4 feline GM-CSF gene (SEQ ID NOs: 9 and 10).

FIG. 9: Table of the cross-serum neutralization titers.

Figure 3:
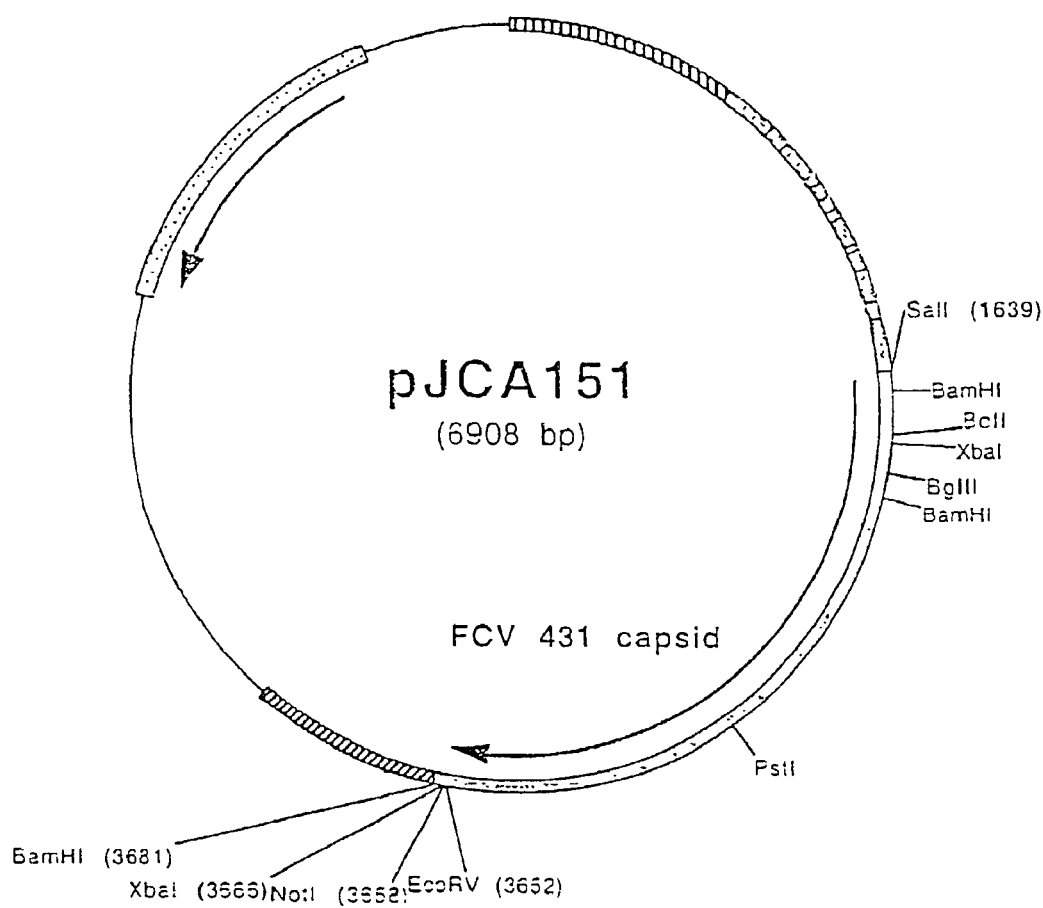
FIG. 3: Restriction Map of the plasmid pJCA151.

The invention essentially relates to two FCV strains obtained by pharyngeal swabs taken in France and the United Kingdom on cats exhibiting signs of infection by feline caliciviruses. They are respectively strain G1 (deposited at the Collection Nationale de Cultures de Microorganismes (or CNCM) of Institut Pasteur, Paris, France, under the accession number I-2167) and strain 431 (deposited at the CNCM under the accession number I-2166), both deposited on Mar. 12, 1999. This FCV G1 strain isolated in France does not correspond to the FCV strain isolated in the United Kingdom in 1978 by Tohya (Tohya Y. et al. Jpn. J. Sci., 1990, 52, 955–961) and also called G1.

The selection of the FCV 431 and G1 strains was carried out by cross-serum neutralization tests with respect to the FCV isolates of a reference panel. This reference panel is composed of 18 current isolates of FCV taken from cats exhibiting signs of infection with feline calicivirus and coming from three distinct geographical regions. 7 isolates are American, these isolates are identified RMI1, RMI2, RMI3, RMI5, RMI6, RMI7 and RMI9. 7 isolates are French, they are designated A2, F1, G1, G3, F3031, H3-2 and H1-4. The last 4 isolates are English, they are designated 431, 388b, 337 and J5.

The panel strains are accessible from the Applicant simply on request. They have also been published in a review article "Archives of Virology" (Poulet et al. Arch. Virol. February 2000. 145(2). 243–261), available online on Internet on the date of filing with the editor.

During cross-serum neutralization tests between 18 FCV isolates of the reference panel, it was found, surprisingly, that the antiserum for isolate 431 neutralizes 14 of the 17 heterologous isolates of the reference panel (the homologous serum neutralization titer is not taken into account). By comparison, the antisera for the "historical" vaccine strains 255 and F9 neutralize only 2 of the 18 panel isolates each.

Unexpectedly, the Applicant has therefore found with the FCV 431 strain a dominant strain which can be used for the protection of the Felidae and in particular of cats against most FCV strains. By virtue of the panel of FCV strains disclosed here, it is possible for persons skilled in the art to select other dominant FCV strains. By way of equivalence, the invention also covers through the FCV 431 strain the FCV strains which are equivalent thereto, which have antibodies with broad cross-neutralization spectrum.

Equivalence exists when the antiserum for an FCV strain seroneutralizes at least 13 of the 18 heterologous isolates of the reference panel (that is to say including FCV 431), preferably when it seroneutralizes at least 14 of the 18 heterologous isolates of the reference panel, still more preferably when it seroneutralizes at least 15 of the 18 heterologous isolates of the reference panel.

It is generally considered that an FCV strain seroneutralizes another FCV strain when the heterologous serum neutralization titer is greater than or equal to $1.2 \log_{10} VN_{50}$ (Povey C. and Ingersoll J., Infection and Immunity, 1975, 11, 877–885). The Applicant took this value as the positivity threshold. However, the cross-serum neutralization results obtained with an FCV isolate having a homologous serum neutralization titer of less than or equal to $2 \log_{10} VN_{50}$ cannot be interpreted.

A second method for establishing the equivalence of an FCV strain with respect to the FCV 431 strain is to use monoclonal antibodies specific for the FCV 431 strain and to test the candidate FCV strain by indirect immunofluorescence (IIF). The Applicant has thus succeeded in producing several monoclonal antibodies which have proved specific for the 431 strain. One of them was called 44. There is equivalence if there is reactivity in immunofluorescence with monoclonal antibodies specific for 431, for example with the monoclonal antibody 44. This monoclonal antibody and the corresponding hybridoma are available from the Applicant upon simple request and are also disclosed in the article by Poulet et al., supra. The corresponding hybridoma was also deposited on 11 Aug. 1999 at the CNCM under the accession number I-2282. It goes without saying, however, that persons skilled in the art are perfectly capable of producing monoclonal antibodies by conventional techniques and of selecting, relative to the panel, those which are specific for the 431 strain.

The other FCV G1 strain was chosen for its complementarity to the FCV 431 strain, namely that the combination of the antisera for 431 and for G1 seroneutralize 100% of the isolates of the reference panel, that is to say that the FCV G1 strain has a homologous serum neutralization titer greater than or equal to $2 \log_{10} VN_{50}$ and heterologous serum neutralization titers greater than or equal to $1.2 \log_{10} VN_{50}$ with respect to the FCV isolates of the reference panel against which the 431 antiserum does not seroneutralize or seroneutralizes weakly (value less than $1.2 \log_{10} VN_{50}$) The invention also covers the equivalent FCV strains having the same complementarity with respect to the FCV 431 strain. It is also possible to produce and select antibodies specific for this strain, which makes it possible to determine equivalents on this other basis.

The Applicant has, in addition, succeeded in isolating, characterizing and sequencing the gene for the capsid of FCV 431 and FCV G1, the capsid protein, and has determined the corresponding cDNA (complementary DNA) sequences.

Figure 2:
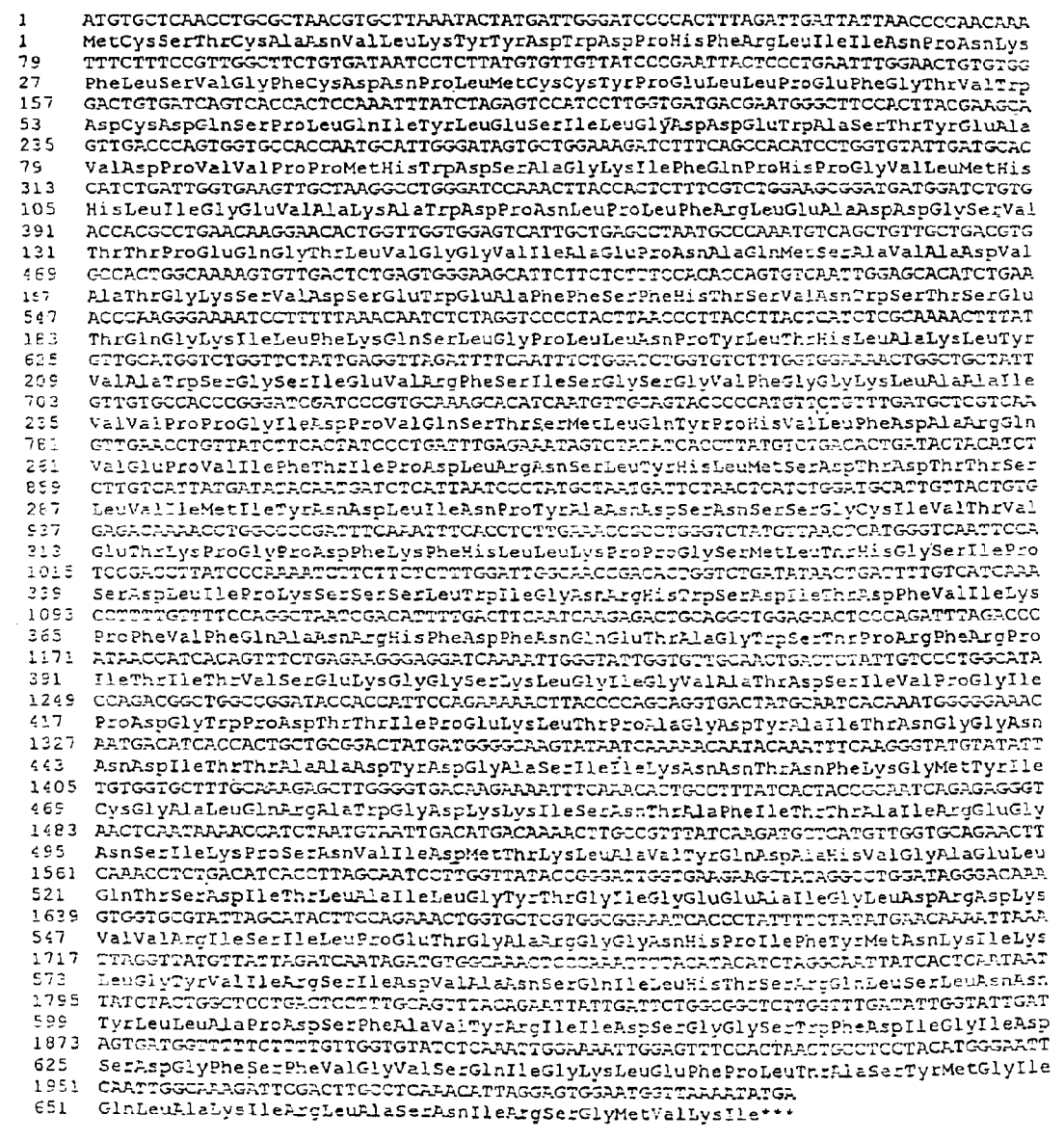

The subject matter of the invention is therfore a nucleic acid fragment comprising all or part of the nucleotide sequence encoding the capsid protein of the 431 virus whose amino acid sequence is represented in SEQ ID NO: 4 or in FIG. 2, or an immunologically active fragment of this protein, that is to say an epitope, peptide or polypeptide of the capsid protein.

The subject matter of the invention is in particular a DNA fragment comprising the cDNA sequence of SEQ ID NO: 3 or a fragment conserving the essential properties of the complete sequence, that is to say encoding a peptide, polypeptide or epitope substantially conserving the immunogenic activity of the capsid protein. The subject of the invention is in particular a DNA fragment comprising this cDNA sequence, which is in particular coupled with elements for the regualtion of transcription.

The subject of the invention is in particular a DNA fragment comprising the cDNA sequence of SEQ ID NO: 6 or a fragment conserving the essential properties of the complete sequence, that is to say encoding a peptide, polypeptide or epitope substantially conserving the immunogenic activity of the capsid protein. The subject of the invention is in particular a DNA fragment comprising this cDNA sequence, which is in particular coupled with elements for the regulation of transcription.

It goes without saying that the invention automatically covers the nucleic acid fragments, DNA fragments and cDNA sequences which are equivalent, that is to say the nucleotide fragments and sequences specific for the FCV capsid which do not change the functionality or the strain specificity of the described sequence or of the polypeptides encoded by this sequence. The sequences which differ by degeneracy of the code will of course be included.

The invention also automatically covers the nucleotide sequences (RNA, DNA, cDNA) which are equivalent in the sense that they encode an FCV capsid protein, or a specific peptide, polypeptide or epitope of FCV capsid protein, which is capable of inducing in vivo in the feline species, in particular in cats, antibodies having substantially the same cross-neutralization as the antiserum for the FCV 431 strain. They are in particular the sequences obtained from equivalent FCV strains according to the definition given above with respect to the panel and/or the monoclonal antibody 44.

Figure 1:
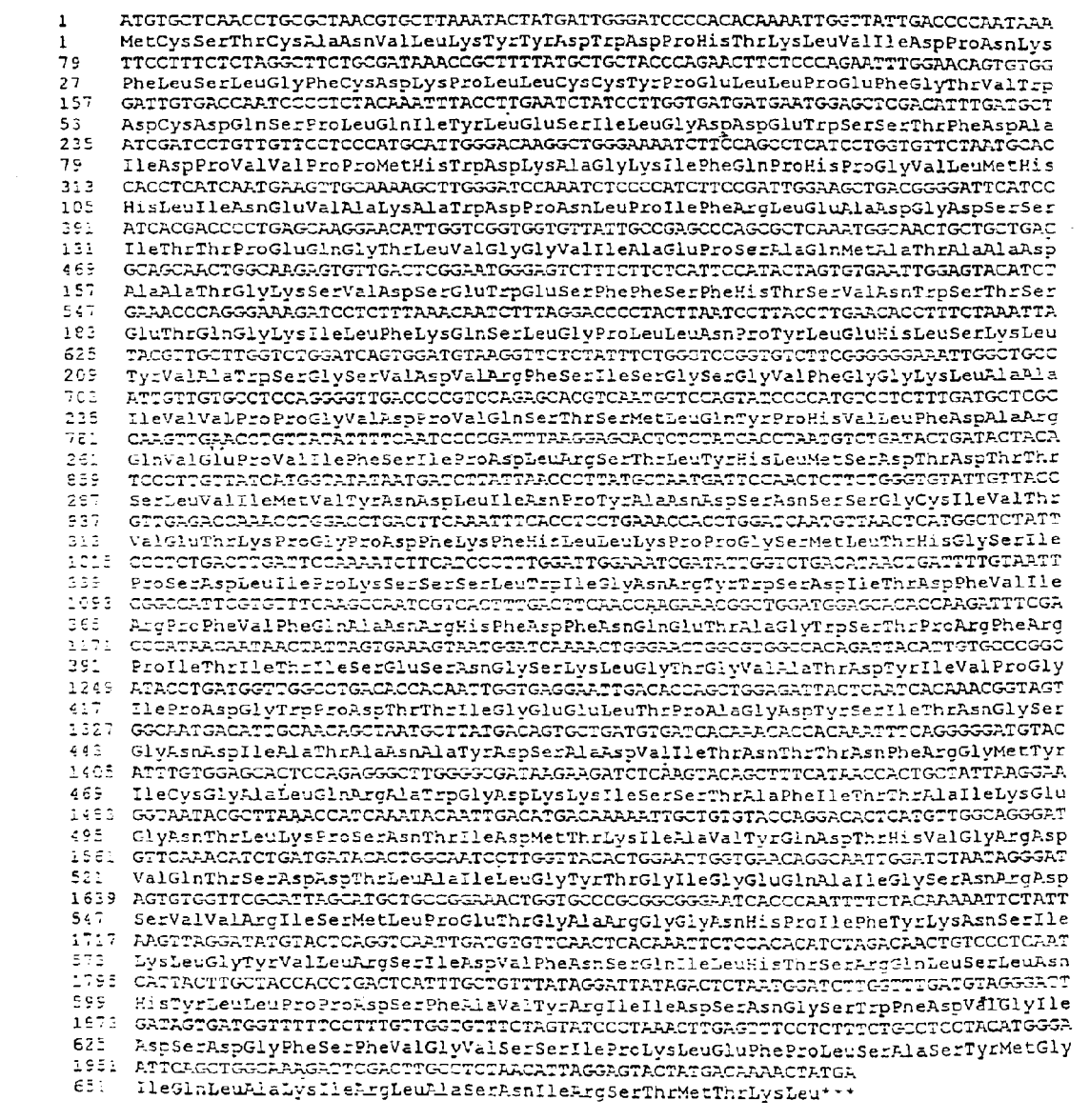

The subject of the invention is also a nucleic acid fragment comprising all or part of the nucleotide sequence encoding the G1 virus capsid protein as represented in SEQ ID NO: 2 or in FIG. 1, or an immunologically active fragment of this protein, that is to say an epitope, peptide or polypeptide substantially conserving the immunogenic activity of the capsid protein.

The subject of the invention is in particular a DNA fragment comprising the cDNA sequence of SEQ ID NO: 1 or a fragment conserving the essential properties of the complete sequence, that is to say encoding a peptide, polypeptide or epitope substantially conserving the immunogenic activity of the capsid protein. The subject of the invention is in particular a DNA fragment comprising this cDNA sequence, in particular coupled with elements for the regulation of transcription. It goes without saying that the invention automatically covers the nucleic acid fragments, DNA fragments and cDNA sequences which are equivalent, that is to say the nucleotide fragments and sequences which do not change the functionality or the strain specificity of the sequence described or of the polypeptides encoded by this sequence. The sequences which differ by degeneracy of the code will of course be included.

The invention also automatically covers the nucleotide sequences (RNA, DNA, cDNA) which are equivalent in the sense that they encode a peptide, polypeptide or epitope capable of inducing in vivo in the feline species, in particular in cats, antibodies having substantially the same cross-neutralization spectrum as the antiserum for the FCV G1 strain. They are in particular nucleotide sequences obtained from FCV strains which are complementary in the sense given above.

The gene encoding the capsid protein of the FCV G1 and FCV 431 viruses has a size of 2007 nucleotides for FCV 431 and 2010 nucleotides for FCV G1. The capsid protein has a size of 668 amino acids for FCV 431 and of 669 amino acids for FCV G1, and a mass of 60–65 kDa (protein p65).

The subject of the invention is also an expression vector comprising at least one DNA fragment according to the invention, in particular a type 431 cDNA or a type G1 cDNA, under conditions allowing its expression in vivo. According to a specific feature, the expression vector comprises a type 431 cDNA and a type G1 cDNA. "Type" should be understood to mean that the cDNA is complementary to an RNA sequence of the strain considered.

These expression vectors may be poxviruses, for example the vaccinia virus, avipoxes (canarypox, fowlpox), including the species-specific poxviruses (swine pox, raccoonpox and camelpox), adenoviruses and herpesviruses, such as the feline herpesviruses (e.g. FR-A-2 741 806). For the poxviruses, persons skilled in the art can refer to WO-A-9215672, WO-A-9526751, WO-A-9012882 and WO-A-9527780; U.S. Pat. Nos. 6,004,777; 5,990,091; 5,989,561; 5,843,456.

Several insertion strategies may be used for the expression of several heterologous nucleotide sequences from the same expression vector in vivo. These insertion strategies are in particular the use of a double expression cassette having an opposite orientation, or the use of a double expression cassette having an identical orientation, or alternatively a multiple expression cassette having an "IRES" (Internal Ribosome Entry Site) element situated between each insert (Patent EP-A1-0803573).

The heterologous nucleotide sequences are inserted under the control of signals for the regulation of transcription and in particular of promoters, which are preferably brought during the insertion. It is not however excluded to cause these heterologous nucleotide sequences to be expressed under the control of signals which are specific to the expression vector used. For the canarypox expression vectors, one of the preferred promoters is the H6 vaccinia promoter (Taylor J. et al. Vaccine, 1988, 6, 504–508; Guo P. et al. J. Virol., 1989, 63, 4189–4198; Perkus M. et al. J. Virol., 1989, 63, 3829–3836).

The in vivo expression vectors may also be plasmids. The term plasmid is intended to cover any DNA transcription unit in the form of a polynucleotide sequence comprising a cDNA sequence according to the invention and the elements necessary for its expression in vivo. The circular plasmid form, supercoiled or otherwise, is preferred. The linear form also falls within the scope of this invention.

Each plasmid comprises a promoter capable of ensuring, in the host cells, the expression of the cDNA inserted under its control. It is in general a strong eukaryotic promoter in particular an early cytomegalovirus promoter CMV-IE, of human or murine origin, or possibly of another origin such as rats or guinea pigs. More generally, the promoter is either of viral origin or of cellular origin. As viral promoter other than CMV-IE, there may be mentioned the early or late promoter of the SV40 virus or the LTR promoter of the Rous Sarcoma virus. As cellular promoter, there may be mentioned the promoter of a cytoskeletal gene, such as for example the desmin promoter or alternatively the actin promoter. A subfragment of these promoters, which conserves the same promoter activity is included in the present invention, e.g. the truncated CMV-IE promoters according to WO-A-98/00166.

When several heterologous sequences (cDNA and/or genes of FCV or of other feline pathogens) are present in the same plasmid, these may be present in the same transcription unit or in two different units.

The plasmids may also comprise other elements for regulation of transcription, such as for example stabilizing sequences of the intron type, preferably intron II of the rabbit β-globin gene (van Ooyen et al. Science, 1979, 206: 337–344), signal sequence of the protein encoded by the gene for tissue plasminogen activator (tPA; Montgomery et al. Cell. Mol. Biol. 1997, 43: 285–292), and polyadenylation signal (polyA), in particular of the gene for bovine growth hormone (bGH) (U.S. Pat. No. 5,122,458) or of the rabbit β-globin gene.

The subject of the invention is also the use of the cDNAs according to the invention for the in vitro production of capsid proteins or of their fragments and immunologically active epitopes and their incorporation into immunogenic preparations and subunit vaccines.

The subject of the invention is also an immunogenic preparation or vaccine against feline calicivirosis comprising at least one recombinant in vivo expression vector according to the invention and a veterinarily acceptable vehicle or excipient, and optionally an adjuvant.

The notion of immunogenic preparation covers any preparation capable, once administered to cats, of inducing at least an immune response directed against the feline pathogen considered. Vaccine is understood to mean a preparation capable of inducing effective protection.

Preferably, this immunogenic preparation or this vaccine comprises an in vivo expression vector into which is inserted a type FCV 431 cDNA, which includes its equivalents or an FCV G1 cDNA, which includes the equivalents of the latter.

According to a first very advantageous characteristic feature, this immunological preparation or this vaccine comprises an expression vector into which is inserted an FCV 431 type cDNA, which includes its equivalents, and an FCV G1 type cDNA, which also includes the equivalents of the latter.

According to a second very advantageous specific feature, this immunological preparation or this vaccine comprises at least two expression vectors: in the first is inserted an FCV 431 type cDNA, which includes its equivalents, and in the second a cDNA of the FCV G1 strain, which also includes the equivalents of the latter.

To supplement the preparations and vaccines in accordance with the invention with adjuvants, it is possible to use any appropriate adjuvant known to persons skilled in the art. However, it is preferable either to formulate them in the form of oil-in-water emulsions, or to add to them polymers of acrylic or methacrylic acid or copolymers of maleic anhydride and of alkenyl derivative, or alternatively a cationic lipid containing a quaternary ammonium salt.

Among the polymers, the polymers of acrylic or methacrylic acid which are crosslinked, in particular with polyalkenyl ethers of sugars or polyalcohols, are preferred. These compounds are known under the term carbomer (Pharmeuropa vol. 8, No. 2, June 1996). Persons skilled in the art can also refer to U.S. Pat. No. 2,909,462 (incorporated by way of reference) describing such acrylic polymers crosslinked with a polyhydroxylated compound having at least 3 hydroxyl groups, preferably not more than 3, the hydrogen atoms of at least three hydroxyls being replaced with unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents, such as methyl. The products sold under the name Carbopol® (BF Goodrich, Ohio, USA) are particularly appropriate. They are crosslinked with an allyl sucrose or with allylpentaerythritol. Among them, there may be mentioned Carbopol® 974P, 934P and 971P.

Among the copolymers of maleic anhydride and of alkenyl derivative, the EMA® copolymers (Monsanto) which are copolymers of maleic anhydride and of ethylene, which are linear or crosslinked, for example crosslinked with divinyl ether, are preferred. Reference may be made to J. Fields et al., Nature, 186: 778–740, 4 Jun. 1960 (incorporated by way of reference). From the point of view of their structure, the polymers of acrylic or methacrylic acid and the EMA® copolymers are preferably formed of basic units of the following formula:

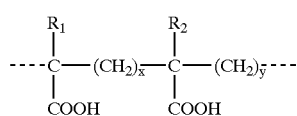

in which:
$R_1$ and $R_2$, which are identical or different, represent H or $CH_3$
x=0 or 1, preferably x=1
y=1 or 2, with x+y=2

For the EMA® copolymers, x=0 and y=2. For the carbomers, x=y=1.

These polymers are dissolved in water or in physiological saline (NaCl at 20 g/l) and the pH is adjusted to 7.3–7.4 with sodium hydroxide, to give the adjuvant solution into which the expression vector or the subunits will be incorporated.

The concentration of polymer in the final vaccine composition will be from 0.01% to 1.5% W/V, more particularly from 0.05 to 1% W/V, preferably from 0.1 to 0.4% W/V.

The cationic lipids containing a quaternary ammonium salt, which are particularly but not exclusively suitable for the plasmid expression vectors correspond to the formula:

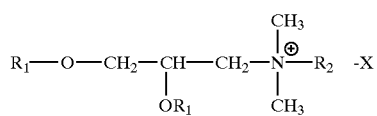

in which R1 is a saturated or unsaturated, linear aliphatic radical having from 12 to 18 carbon atoms, R2 is another aliphatic radical containing 2 or 3 carbon atoms, and X is a hydroxyl or amine group.

DMRIE (N-(2-hydroxyethyl)-N,N-dimethyl-2,3-bis (tetradecyloxy)-1-propanammonium; WO-A-9634109), preferably coupled with a neutral lipid, in particular DOPE (dioleoyl-phosphatidyl-ethanolamine), to form DMRIE-DOPE, is preferred. Preferably, the plasmid is mixed with this adjuvant immediately before use and it is preferable, before its administration to the animal, to allow the mixture thus prepared time to form a complex, for example for a period ranging from 10 to 60 minutes, in particular of the order of 30 minutes.

When DOPE is present, the DMRIE:DOPE molar ratio ranges preferably from 95:5 to 5:95, more particularly 1:1.

The plasmid:adjuvant DMRIE or DMRIE-DOPE weight ratio may range in particular from 50:1 to 1:10, in particular from 10:1 to 1:5, preferably from 1:1 to 1:2.

Figure 5:
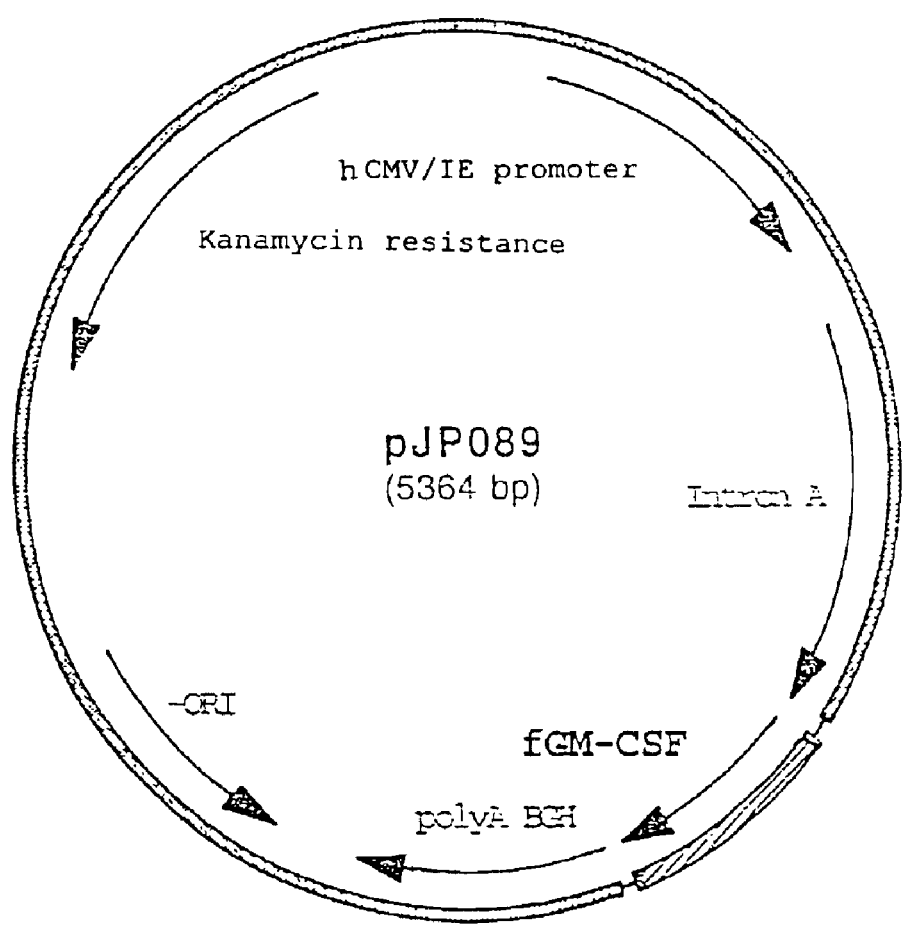
FIG. 5: Restriction Map of the plasmid pJP089.

The in vivo expression vectors encoding an FCV type cDNA according to the invention may also encode feline GM-CSF or may be combined with a second vector encoding feline GM-CSF (e.g. the plasmids pJP089 and pJP090, FIG. 5 and FIG. 6 respectively). In the case of plasmids, a mixture of two plasmids is preferred. In the case of viral vectors, a single vector is preferred. This expression vector or this mixture of expression vectors may also be supplemented with adjuvant as described above.

The subject of the invention is also a multivalent immunogenic preparation or a multivalent vaccine against feline calicivirosis and against at least one other feline pathogen, using the same recombinant in vivo expression vector containing and expressing at least one FCV type cDNA according to the invention and at least one nucleotide sequence of an immunogen or another feline pathogen or of an immunologically active fragment of this immunogen.

The subject of the invention is also a multivalent immunogenic preparation or a multivalent vaccine comprising at least one in vivo expression vector into which is inserted at least one FCV type cDNA according to the invention and at least a second expression vector into which is inserted a sequence encoding an immunogen, or an immunologically active fragment, of another feline pathogen. Appropriate plasmids into which is inserted a sequence encoding an immunogen, or an immunologically active fragment, of another feline pathogen, may be in particular those described in Examples 7 to 15 and 17 to 19 of Patent Application WO-A-9803660 (pPB179, pPB180, pPB181, pAB009, pAB053, pAB052, pAB056, pAB058, pAB029, pAB030, pAB083, pAB041).

The monovalent or multivalent recombinant vaccines as described above may also be combined with at least one conventional vaccine (inactivated, attenuated live, subunit) directed against at least one feline pathogen which is identical or different.

Said other feline pathogens are in particular chosen from the group comprising the feline rhinotrachitis virus or the feline herpesvirus (FHV), the feline leukemia virus (FeLV), the feline parvoviruses (FPV), the feline infectious peritonitis virus (FIPV), the feline immunodeficiency virus (FIV), the rabies virus, *Chlamydia*.

The subject of the invention is also the isolated, purified or synthetic capsid proteins of the FCV G1 strain and of the FCV 431 strain, having an amino acid sequence represented in SEQ ID Nos: 2 and 4 respectively. This automatically covers the equivalent proteins, that is to say the proteins derived from strains which are equivalent to the FCV 431 and FCV G1 strains according to the definitions given above (use of the panel and/or of a monoclonal antibody, in particular the monoclonal antibody 44). Advantageously, these capsid proteins may be assembled in the form of empty capsids.

The subject of the invention is also the fragments and epitopes (at least about 8 to 10 amino acids) of these proteins, which conserve the specificity and immunogenicity of the whole protein.

The capsid proteins, optionally assembled in the form of empty capsids, and their fragments and epitopes, may be produced by expression in vitro. The corresponding nucleotide sequence is inserted into an in vitro expression system and expressed by this system, and the product of expression harvested and optionally purified, as is known per se.

The expression system may be of viral origin, in particular the baculovirus (U.S. Pat. No. 4,745,051). The coding sequence or a fragment (in the case of the epitope or of the fragment) is integrated into the baculovirus genome (e.g. the baculovirus *Autographa californica* Nuclear Polyhedrosis Virus AcNPV) and the latter is then propagated, in particular in insect cells, e.g. *Spodoptera frugiperda* Sf9 (deposit ATCC CRL 1711).

The in vitro expression system may be of prokaryotic origin, e.g. *Escherichia coli*, or of eukaryotic origin, in particular yeasts, e.g. *Saccharomyces cerevisiae*, or mammalian eukaryotic cells, in particular cell lines such as CHO (hamster ovary cells), HeLa, BHK or insect cells, e.g. *Spodoptera frugiperda* (supra), or alternatively feline cells.

As promoters which can be used in these cellular constructs, there may be mentioned the strong viral promoters such as those of the SV40 virus (Fiers et al., Nature, (1978) 273:113) and the early promoter (CMV-IE) of the human CMV virus or cytomegalovirus (McGregor and Caskey, Nucleic Acids Res. 17:2365, 1989) or of murine or other origin, or alternatively that of the polyhedrin gene of the baculovirus AcNPV (Hooft van Iddekinge et al., 1983, Virology 131:561–565).

Persons skilled in the art know how to purify and/or isolate the proteins, assembled or otherwise in the form of empty capsids, their fragments and epitopes from the product of the techniques described above. By way of example, it can be recalled that persons skilled in the art have at their disposal various methods which comprise in particular: precipitation based on the solubility of the proteins, fragments and epitopes of interest according to the saline conditions of the medium, precipitation with organic solvents, polymers or other materials, affinity precipitation and selective denaturation, column chromatography, including high-performance liquid chromatography (HPLC), ion-exchange chromatography, affinity chromatography, immunoaffinity chromatography, chromatography using ligands, immunoprecipitation, gel filtration, electrophoresis, filtration methods, in particular ultrafiltration, and gradient ultracentrifugation.

Persons skilled in the art can refer by way of example to K. Y. Green et al., J. Clin. Microb., July 1997, Vol 35, 7:1909–1914, for the production of capsids in baculovirus propagated on Sf9 cells and harvested by ultracentrifugation on sucrose gradients (10 to 50%).

The capsid proteins, and their fragments and epitopes, may also be produced by chemical synthesis by the methods available to persons skilled in the art.

The subject of the invention is also the immunogenic preparations and vaccines comprising at least one subunit antigen formed of a capsid protein, preferably assembled in the form of empty capsids, of FCV 431 and/or FCV G1, or of a corresponding fragment or epitope, in a veterinarily acceptable vehicle or excipient, and preferably an adjuvant. Preferably, the preparations and vaccines according to the invention comprise subunit antigens derived from the two strains FCV 431 and FCV G1. Likewise, the preparations and vaccines may comprise nonassembled capsid proteins and proteins assembled in the form of empty capsids.

To supplement the subunit vaccines and immunogenic preparations according to the invention with adjuvants, it is possible to use as adjuvant (1) aluminum hydroxide, (2) a polymer of acrylic or methacrylic acid, a polymer of maleic anhydride and of alkenyl derivative (which are described above), or (3) to formulate the immunogenic preparation or vaccine in the form of an oil-in-water emulsion, in particular the emulsion SPT described p 147 "Vaccine Design, The Subunit and Adjuvant Approach" edited by M. Powell, M. Newman, Plenum Press 1995, and the emulsion MF59 described p 183 in the same book.

The oil-in-water emulsion may in particular be based on light liquid paraffin oil (European Pharmacopeia type), isoprenoid oil such as squalane, squalene; oil resulting from the oligomerization of alkenes, in particular of isobutene or of decene; esters of acids or alcohols containing a linear alkyl group, more particularly vegetable oils, ethyl oleate, propylene glycol di(caprylate/caprate), glyceryl tri(caprylate/caprate), propylene glycol dioleate; esters of branched fatty alcohols or acids, in particular esters of isostearic acid. The oil is used in combination with emulsifiers to form the emulsion. The emulsifiers are preferably nonionic surfactants, in particular the esters of sorbitan, mannide, glycerol, polyglycerol, propylene glycol and of oleic, isostearic, ricinoleic or hydroxystearic acid, which are optionally ethoxylated, the polyoxypropylene-polyoxyethylene block copolymers, in particular the Pluronic® copolymers, especially L121.

The subject of the invention is also the multivalent vaccines and immunogenic preparations in which the FCV valency is a subunit valency as described above.

The subject of the present invention is also a method of immunizing cats against diseases caused by the feline calicivirosis viruses.

This method comprises the administration of an immunological preparation or of a vaccine according to the invention to cats. This administration may be made in particular by the parenteral route, by subcutaneous, intradermal, intramuscular or intraperitoneal administration. Preferably, the administration is made by the subcutaneous or intramuscular route.

Various means of administration may be used for the plasmid vaccines and immunogenic preparations, in particular gold particles coated with DNA and discharged so as to penetrate into the cells of the skin of the subject to be immunized (Tang et al. Nature 1992. 356. 152–154) and liquid-jet injectors which make it possible to transfect both skin cells and cells of the underlying tissues (Furth et al. Analytical Bioch. 1992. 205, 365–368).

Persons skilled in the art possess the necessary competence to precisely define the number of administration and the doses to be used for each immunization protocol.

The invention will now be described in greater detail with the aid of the embodiments taken by way of nonlimiting examples and referring to the drawing in which:

EXAMPLES

All the constructions of plasmids were carried out using standard molecular biology techniques (cloning, digestion with restriction enzymes, synthesis of a single-stranded complementary DNA, polymerase chain amplification, extension of an oligonucleotide with a DNA polymerase and the like) described by Sambrook J. et al. (*Molecular Cloning: A Laboratory Manual.* $2^{nd}$ Edition. Cold Spring Harbor Laboratory Press. Cold Spring Harbor. N.Y. 1989). All the restriction fragments used for the present invention, as well as the various polymerase chain amplification (PCR) fragments were isolated and purified using the "Geneclean7" kit (BIO101 Inc. La Jolla, Calif.).

Example 1

Isolation and Culture of Feline Calicivirus G1 and 431 Strains

The feline calicivirus strain designated G1 was obtained from a sample collected in France on a cat exhibiting signs of calicivirosis. This FCV G1 strain was deposited on 12 Mar. 1999 at the Collection Nationale de Cultures de Microorganismes (or CNCM) of Institut Pasteur, Paris, France, under the accession number I-2167.

The feline calicivirus strain designated 431 was isolated from a sample taken in England on a cat exhibiting signs of calicivirosis. This FCV 431 strain was deposited on Mar. 12, 1999 at the Collection Nationale de Cultures de Microorganismes (or CNCM) of Institut Pasteur, Paris, France, under the accession number I-2166.

For their amplification, the feline calicivirus strains were cultured on cells of the cat kidney line (Crandell-Reese Feline Kidney or CRFK, No. ATCC CCL-94, Crandell et al. In Vitro 1973, 9, 176–185).

The CRFK cells are cultured in a 96-well plate or in a 25-$cm^2$ Falcon with DMEM medium supplemented with 5% fetal calf serum containing about 100,000 cells per ml. The cells are cultured at +37° C. in an atmosphere containing 5% $CO_2$.

After 3 days, the cell layer arrives at confluence. The culture medium is then replaced with serum-free DMEM medium but supplemented with 50 mg/l of gentamycin and the FCV viral isolates are added in an amount of a volume of 100 μl of four-fold serial dilutions per well for the cloning in limiting dilutions of the FCV viruses or of 1 ml per Falcon.

When the cytopathic effect (CPE) is complete (24–48 hours after the start of the culture), the viral suspensions are harvested and frozen at −70° C. 3 to 4 successive passages are generally necessary for the production of a viral batch. The viral batch is stored at −70° C.

Example 2

Extraction of the Viral RNA of the Feline Calicivirus G1 and 431 Strains

The CRFK cells are cultured at 37° C. in 2-liter roller flasks (850 $cm^2$) in modified Eagle's medium (MEM, Gibco BRL) supplemented with 2.5% of lactalbumin hydrolysate (Gibco BRL) and 5% fetal calf serum (Gibco BRL). 300 ml of a cellular suspension in MEM medium containing about 100,000 cells/ml are added per roller flask. After 3 days, the cell layer becomes confluent. The cell culture medium is then replaced with serum-free MEM medium and the FCV virus added at a multiplicity of infection (mol) of 0.5 $CCID_{50}$/cell. The viral culture is maintained at 37° C. for 24 to 48 hours until a cytopathic effect is obtained for the whole cellular lawn. The viral suspension is harvested and then clarified by centrifugation.

The viral RNA contained in 100 ml of viral suspension of the FCV G1 strain, which has just been prepared, was extracted with the solutions of the kit "High Pure™ Viral RNA Kit" Cat # 1 858 882, Roche Molecular Biochemicals), according to the supplier's instructions for the extraction steps. The RNA pellet obtained at the end of the extraction was resuspended with 10 ml of RNase-free sterile distilled water.

The viral RNA of the FCV 431 strain was extracted under the same conditions from 100 ml of viral suspension of the corresponding strain. The RNA pellet obtained at the end of the extraction was resuspended with 10 ml of RNase-free sterile distilled water.

Example 3

Synthesis of the DNAs Complementary to the Capsid Genes of the Feline Calicivirus G1 and 431 Strains The complementary DNAs corresponding to the capsid genes of the feline calicivirus G1 and 431 strains were synthesized with the kit "Gene Amp RNA PCR Kit" (Cat #

N 808 0017, Perkin-Elmer, Norwalk, Conn. 06859, USA) using the conditions given by the supplier.

For the FCV G1 strain, a reverse transcription reaction, followed by a polymerase chain reaction ("RT-PRC" reaction) was carried out with 1 ml of the suspension of FCV G1 viral RNA (Example 2) and with the following oligonucleotides:
PB331 (33 mer) (SEQ ID NO 11)
5'TTGCGGCCGCTGTGATGTGTTCGAATTTGAG3'
and PB333 (36 mer) (SEQ ID NO 12)
5'TTGGCGCCGYTGACCMAGTGCAGCYTTRTCCAATTC3'

The conditions for the synthesis of the first complementary DNA strand are a temperature of 42° C. for 15 min, then 99° C. for 5 min, and finally 4° C. for 5 min. The conditions for the PCR reaction are a temperature of 95° C. for 2 min, then 35 cycles (95° C. for 1 min, then 62° C. for 1 min, and 72° C. for 2 min), and finally 72° C. for 7 min in order to produce an RT-PCR fragment of about 2000 base pairs (bp) which was identified "G1-4".

For the FCV 431 strain, a reverse transcription reaction, followed by a polymerase chain reaction ("RT-PCR" reaction) was carried out with 1 ml of the suspension of FCV 431 viral RNA (Example 2) and with the following oligonucleotides:
PB331 (33 mer) (SEQ ID NO 11)
and PB332 (38 mer) (SEQ ID NO 13)
5'TTGGCGCCAAYWGTRTTWGHTACAGTRTCAATYARRCC3'

The conditions for the synthesis of the first complementary DNA strand are a temperature of 42° C. for 15 min, then 99° C. for 5 min, and finally 4° C. for 5 min. The conditions for the PCR reaction are a temperature of 95° C. for 2 min, then 35 cycles (95° C. for 1 min, then 62° C. for 1 min, and 72° C. for 2 min), and finally 72° C. for 7 min in order to produce an RT-PCR fragment of about 2000 base pairs (bp) which was identified "431-2".

Example 4

Cloning of the Gene Encoding the Capsid Protein of the Feline Calicivirus G1 Strain The RT-PCR fragment "G1-4" was digested with NarI and then with NotI in order to isolate, after agarose gel electrophoresis, the NarI-NotI fragment of about 2000 bp. This fragment was ligated with the vector pBlueScript® II KS+ (Cat # 212208 Stratagene Inc., La Jolla, Calif. 92037, USA), previously digested with NotI and ClaI, and then dephosphorylated, to give the plasmid pG1-4-5 (5033 bp).

The NotI-NarI fragment cloned into this plasmid was completely sequenced on both strands in order to determine the sequence of the capsid gene. The sequence of the capsid gene of the FCV G1 strain (2010 bp) (SEQ ID NO 1), as well as the sequence of the capsid protein (p65) (668 amino acids) (SEQ ID NO 2) encoded by this gene, are presented in FIG. 1.

Example 5

Cloning of the Gene Encoding the Capsid Protein of the Feline Calicivirus 431 Strain The RT-PCR fragment "431-2" was digested with NarI and then with NotI in order to isolate, after agarose gel electrophoresis, the NarI-NotI fragment of about 2000 bp. This fragment was ligated with the vector pBlueScript® II KS+ (Cat # 212208 Stratagene Inc., La Jolla, Calif. 92037, USA), previously digested with NotI and ClaI, and then dephosphorylated, to give the plasmid p431-2-1 (4985 bp).

The NotI-NarI fragment cloned into this plasmid was completely sequenced on both strands in order to determine the sequence of the capsid gene. The sequence of the capsid gene of the FCV 431 strain (2007 bp) (SEQ ID NO 3), as well as the sequence of the capsid protein (p65) (668 amino acids) (SEQ ID NO 4) encoded by this gene, are presented in FIG. 2.

Example 6

Construction of the Plasmid pJCA151

A PCR reaction was carried out using plasmid p431-2-1 (Example 5) as template and the following oligonucleotides:
JCA289 SEQ ID NO 14 (36 mer):
5'AAACGCGTCGACATGTGCTCAACCTGCGCTAACGTG3'
and JCA290 SEQ ID NO 15 (33 mer):
5'TTTGATATCTCATATTTAACCATTCCACTCC3' in order to amplify a PCR fragment of about 2030 bp. This fragment was digested with the restriction enzymes SalI and EcoRV in order to isolate, after agarose gel electrophoresis, a SalI-EcoRV fragment of 2014 bp. This restriction fragment was then ligated with the plasmid pVR1012 (Hartikka J. et al. Human Gene Therapy. 1997. 7. 1205–1217), previously digested with SalI and EcoRV, to give the plasmid pJCA151 (6908 bp) (FIG. 3).

Example 7

Construction of the Donor Plasmid for Insertion into the C6L Site of the Canarypox Virus FIG. 4 (SEQ ID NOs 5 and 6) shows the sequence of a 3700 bp fragment of the genomic DNA of the canarypox virus. Analysis of this sequence revealed an open reading frame (ORF) which was called C6L, which starts at position 377 and ends at position 2254. The construction of an insertion plasmid resulting in the deletion of the ORF C6L and in its replacement with a multiple cloning site flanked with signals for termination of transcription and of translation was carried out as described below.

A PCR reaction was carried out using the template consisting of the genomic DNA of the canarypox virus and with the following oligonucleotides:

C6A1 (SEQ ID NO 16) (42 mer):
5'ATCATCGAGCTCGCGGCCGCCTATCAAAAGTCTTAATGAGTT3'
and C6B1 (SEQ ID NO 17) (73 mer):
5'AATTCCTCGAGCTGCAGCCCGGGTTTTTATAGCTAATTAGTCATTTTTTCGTAAGTAAGTATTTTTATTTAA3' in order to isolate a 432 bp PCR fragment (fragment A).

A PCR reaction was carried out using the template consisting of the genomic DNA of the canarypox virus and with the following oligonucleotides:

C6C1 (SEQ ID NO 18) (72 mer)
5'CCCGGGCTGCAGCTCGAGGAATTCTTTTTATTGATTAACTAGTCAAATGAGTATATATAATTGAAAAAGTAA3'
and C6D1 (SEQ ID NO 19) (45 mer)
5'GATGTAGGTACCTTCATAAATACAAGTTTGATTAAACTTAAGTTG3' in order to isolate a PCR fragment of 1210 bp (fragment B).

Fragments A and B were hybridized together in order to serve as template for a PCR reaction carried out with the oligonucleotides C6A1 (SEQ ID NO 16) and C6D1 (SEQ ID NO 19) in order to generate a PCR fragment of 1630 bp. This fragment was digested with the restriction enzymes SacI and KpnI, in order to isolate, after agarose gel electrophoresis, a SacI-KpnI fragment of 1613 bp. This fragment was ligated with the vector pBlueScript® II SK+ (Stratagene, La Jolla, Calif., USA, Cat # 212205), previously digested with the enzymes SacI and KpnI, to give the plasmid pC6L. The sequence of this plasmid was verified by sequencing. This plasmid contains 370 bp of sequences situated upstream of the ORF C6L ("left flanking arm C6"), a vaccinia signal for early termination of transcription, stop codons in the 6 reading frames, a multiple cloning site containing the SmaI, PstI, XhoI and EcoRI restriction sites, and finally 1156 bp of sequences situated downstream of the ORF C6L ("right flanking arm C6").

The plasmid pMP528HRH (Perkus M. et al. J. Virol. 1989. 63. 3829–3836) was used as template to amplify the complete sequence of the H6 vaccinia promoter (GenBank accession no. M28351) with the following oligonucleotides:
JCA291 (SEQ ID NO 20)(34 mer)
5'AAACCCGGGTTCTTTATTCTATACTTAAAAAGTG3'
and JCA292 (SEQ ID NO 21) (43 mer)
5'AAAAGAATTCGTCGACTACGATA-
    CAAACTTAACGGATATCGCG3'
in order to amplify a 149 bp PCR fragment. This fragment was digested with the restriction enzymes SmaI and EcoRI in order to isolate, after agarose gel electrophoresis, a SmaI-EcoRI restriction fragment of 138 bp. This fragment was then ligated with the plasmid pC6L, previously digested with SmaI and EcoRI, to give the plasmid pJCA150.

Example 8

Construction of the Recombinant Virus vCP1710 (Recombinant Canarypox Virus Expressing the Capsid Gene of the FCV 431 Strain)

A PCR reaction was carried out using the plasmid p431-2-1 (Example 5) as template and the following oligonucleotides:
JCA293 (SEQ ID NO 22) (55 mer):
5'AAATCGCGATATCCGTTAAGTTTG-
    TATCGTAATGTGCTCAACCTGCGCTAACGTG3'
and JCA294 (SEQ ID NO 23) (33 mer):
5'TTTTGTCGACTCATATTTTAACCATTCCACTCC3'
in order to amplify a PCR fragment of about 2050 bp. This fragment was digested with the restriction enzymes NruI and SalI in order to isolate, after agarose gel electrophoresis, the NruI-SalI fragment of 2035 bp (fragment A). The plasmid pJCA150 (Example 7) was digested with the restriction enzymes NruI and SalI in order to isolate, after agarose gel electrophoresis, the NruI-SalI restriction fragment of about 4500 bp (fragment B). Fragments A and B were then ligated together to give the plasmid pJCA152.

The plasmid pJCA152 was linearized with NotI, and then transfected into chicken embryo primary cells infected with the canarypox virus (strain ALVAC) according to the calcium phosphate precipitation technique previously described (Panicali and Paoletti Proc. Nat. Acad. Sci. 1982. 79. 4927–4931; Piccini et al. In Methods in Enzymology. 1987. 153. 545–563. Eds. Wu R. and Grossman L. Academic Press). Positive plaques were selected on the basis of hybridization with a radiolabeled probe specific for the capsid gene of the FCV 431 strain. These plaques were subjected to 4 successive cycles of selection/purification of plaques until a pure population was isolated. A plaque which is representative of the in vitro recombination between the donor plasmid pJCA152 and the genome of the canarypox virus ALVAC was then amplified and the recombinant virus stock obtained was designated vCP1710.

Example 9

Construction of the Recombinant Virus vCP1711 (Recombinant Canarypox Virus Expressing the Capsid Gene of the FCV G1 Strain)

A PCR reaction was carried out using the plasmid pG1-4-5 (Example 4) as template and the following oligonucleotides:
JCA293 (SEQ ID NO 22)
and JCA295 (SEQ ID NO 24) (33 mer):
5'TTTTGTCGACTCATAGTTTTGTCATAGTACTCC3'
in order to amplify a PCR fragment of about 2050 bp. This fragment was digested with the restriction enzymes NruI and SalI in order to isolate, after agarose gel electrophoresis, the NruI-SalI fragment of 2035 bp (fragment A). The plasmid pJCA150 (Example 7) was digested with the restriction enzymes NruI and SalI in order to isolate, after agarose gel electrophoresis, the NruI-SalI restriction fragment of about 4500 bp (fragment B). Fragments A and B were then ligated together to give the plasmid pJCA153.

The plasmid pJCA153 was linearized with NotI, and then transfected into chicken embryo primary cells infected with the canarypox virus (strain ALVAC) according to the calcium phosphate precipitation technique previously described (Panicali and Paoletti Proc. Nat. Acad. Sci. 1982. 79. 4927–4931; Piccini et al. In Methods in Enzymology. 1987. 153. 545–563. Eds. Wu R. and Grossman L. Academic Press). Positive plaques were selected on the basis of hybridization with a radiolabeled probe specific for the capsid gene of the FCV G1 strain. These plaques were subjected to 4 successive cycles of selection/purification of plaques until a pure population was isolated. A plaque which is representative of the in vitro recombination between the donor plasmid pJCA152 and the genome of the canarypox virus ALVAC was then amplified and the recombinant virus stock obtained was designated vCP1711.

Example 10

Plasmid Encoding Feline GM-CSF

Cat blood was collected by taking blood in a tube containing EDTA. The mononuclear cells were harvested by centrifugation on a Ficoll gradient, and then cultured in a Petri dish 60 mm in diameter. The cat mononuclear cells were then stimulated with concanavalin A (ConA) (final concentration of about 4 µg/ml) and with phytohemagglutinin (PHA) (final concentration of about 10 µg/ml). After stimulation, the "ConA" and "PHA" lymphoblasts were harvested by scraping the culture dishes, and the total RNA of these cells was extracted using the kit "mRNA isolation kit for White Blood Cells" (Boehringer Mannheim/Roche Cat # 1 934 325).

Figure 7:
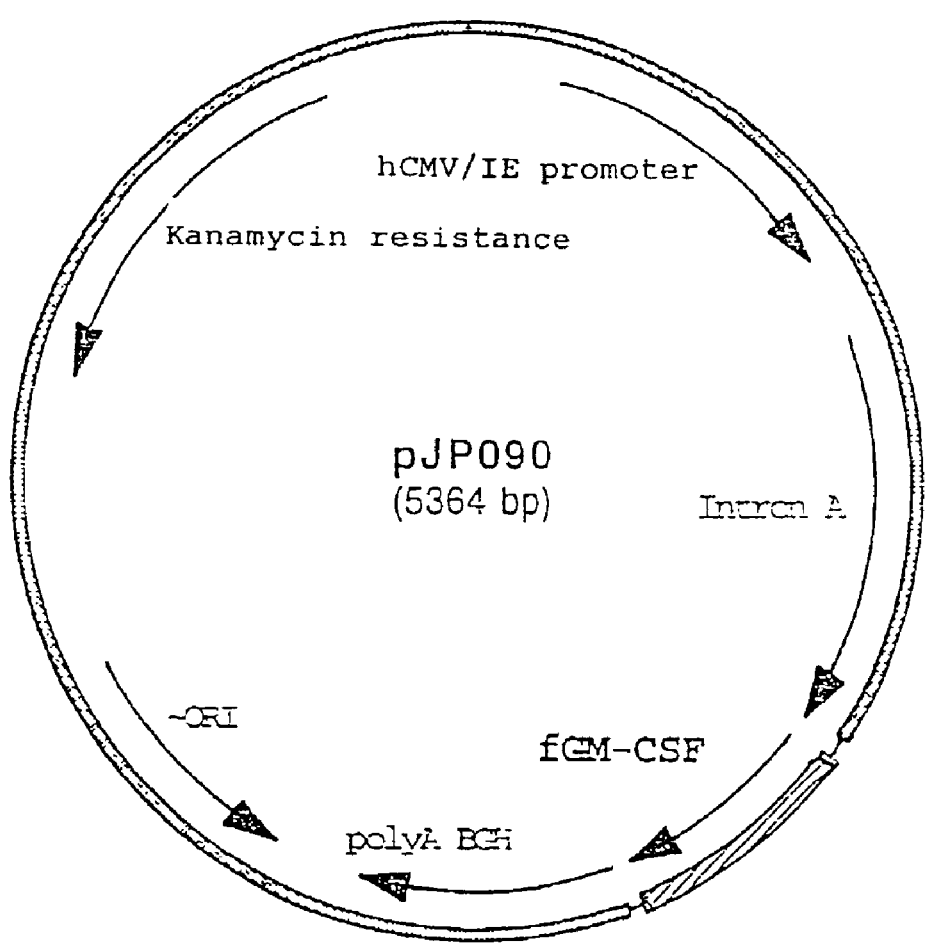
FIG. 7: Restriction Map of the plasmid pJP090.

The total RNA extracted from the cat lymphoblasts stimulated with ConA and PHA served as template for the synthesis of the first strand of complementary DNA. This first strand of complementary DNA was produced by extension of the oligonucleotide p(dT)15 (Boehringer Mannheim/Roche Cat # 814 270). The single-stranded complementary DNA obtained was then used as template for a PCR reaction with the following oligonucleotides:
JP578 (SEQ ID NO 25) (33 mer)
5'TATGCGGCCGCCACCATGTGGCTGCAGAACCTG3' and JP579 (SEQ ID NO 26) (36 mer):
5'TATGCGGCCGCTACGTATCACTTCTTGACTGGTTTC3'
in order to amplify a PCR fragment of about 450 base pairs (bp). This fragment was digested with NotI in order to isolate, after agarose gel electrophoresis, the NotI-NotI fragment of 450 bp. This fragment was then ligated with the plasmid pVR1012 (Hartikka J. et al. Human Gene Therapy. 1997. 7. 1205–1217). Two clones containing the feline GM-CSF sequence (SEQ ID NOs: 7 and 8 and SEQ ID NOs: 9 and 10), in the correct orientation relative to the hCMV/IE promoter were identified pJP089 and pJP090 respectively. These two plasmid have a size of 5364 bp (FIGS. 5 and 7).

The sequence of the feline GM-CSF gene cloned into the plasmid pJP089 contains 13 differences at the nucleotide level with the feline GM-CSF sequence available in GenBank (accession no. AF053007). The most important change is a C→T change which causes a Leucine→Phenylalanine change for the amino acid (first base of the codon for amino acid # 107; FIG. 6). The sequence of the feline GM-CSF gene cloned into the plasmid pJP090 is equivalent to that contained in the plasmid pJP089, except that the Leucine→Phenylalanine change does not exist for amino acid # 107 (FIG. 8). Verification of the 3' sequence of the feline GM-CSF gene by means of the 3'RACE kit showed that, at this position 107, it is possible to have, in the same cat, the amino acid Leucine or the amino acid Phenylalanine.

Example 11

Manufacture of Combined Plasmid Vaccines

The various plasmids necessary for the manufacture of a combined vaccine are mixed. These plasmids may be in particular those described in Examples 6 and 10 (pJCA151, pJP089 and pJP090) and Examples 7 to 15 and 17 to 19 of Patent Application WO-A-9803660 (pPB179, pPB180, pPB181, pAB009, pAB053, pAB052, pAB056, pAB058, pAB029, pAB030, pAB083, pAB041). The mixtures are prepared such that the final concentration of each plasmid corresponds to the effective dose of each plasmid. The solutions which can be used to adjust the final concentration of the vaccine may be either a 0.9% NaCl solution, or PBS buffer.

Example 12

Formulation of the Vaccinal Plasmids

The solution of DNA containing one or more plasmids according to Example 11 is concentrated by ethanol precipitation as described in Sambrook et al. (1989). The DNA pellet is taken up in a 0.9% NaCl solution so as to obtain a concentration of 1 mg/ml. A solution of DMRIE-DOPE at 0.75 mM is prepared by taking up a freeze-dried product of DMRIE-DOPE with a suitable volume of sterile $H_2O$.

The formation of the plasmid DNA-lipid complexes is performed by diluting equal portions of the 0.75 mM DMRIE-DOPE solution with the DNA solution at 1 mg/ml in 0.9% NaCl. The DNA solution is gradually introduced with the aid of a seamed 26G needle along the wall of the vial containing the solution of cationic lipid so as to avoid the formation of foam. Gentle shaking is carried out as soon as the two solutions have been mixed. A composition comprising 0.375 mM of DMRIE-DOPE and 500 µg/ml of plasmid is finally obtained.

It is desirable for all the solutions used to be at room temperature for all the operations described above. The DNA/DMRIE-DOPE complex formation is allowed to take place at room temperature for 30 minutes before immunizing the animals.

Example 13

Formulation of the Vaccinal Canarypox Vectors

For the preparation of vaccines, the recombinant canarypox viruses vCP1710 (Example 8) and vCP1711 (Example 9) may be supplemented with carbomer solutions as adjuvant. The preferred carbomer is Carbopol™ 974P manufactured by BF Goodrich, Ohio, USA (molecular weight of about 3,000,000).

A stock solution containing 1.5% Carbopol™ 974P is initially prepared in distilled water containing 1 g/l of sodium chloride. This stock solution is then used for the preparation of a solution containing 4 mg/ml of Carbopol™ 974P in physiological saline. The stock solution is mixed with a suitable volume of physiological saline, either in a single stage or in several successive stages, the pH value is adjusted at each stage with a 1 N (or alternatively a more concentrated) sodium hydroxide solution in order to obtain a final pH value of 7.3–7.4.

The ready-for-use Carbopol™ 974P solution thus obtained may be used to take up freeze-dried recombinant viruses (e.g. vCP1710, vCP1711) or to dilute concentrated stock solutions of recombinant viruses (e.g. vCP1710, vCP1711). For example, to obtain a viral suspension containing $10^8$ pfu per dose of 1 ml, it is possible to dilute a viral stock solution so as to obtain a titer of $10^{8.3}$ pfu/ml, and then to dilute equal portions with said ready-to-use solution of Carbopol™ 974P at 4 mg/ml.

Example 14

Indirect Immunofluorescence (IIF) Tests

The IIF tests are carried out on 96-well plates containing the CRFK cells cultured in monolayers infected with the FCV viruses to be tested.

200 µl per well of a suspension of CRFK cells containing 90,000 cells/ml in F15 medium (Gibco BRL, Cat # 045-1075) containing 5% of fetal calf serum are cultured in a 96-well plate. At confluence, 320 CCID50 of FCV are inoculated in 100 µl of F15 medium. When the first CPE foci appear, the cells are then rinsed with cold PBS with no calcium or magnesium (PBS, Sigma), and then fixed at −20° C. for 30 minutes with cold acetone containing 5% v/v of water. After drying, the infected and fixed cells are brought into contact for 30 minutes at 37° C. with 100 µl per well of ascitic fluid corresponding to the anti-FCV 431 monoclonal antibody 44 (hybridoma 431 2 0 17 E9 T, deposited at the CNCM under the accession number I-2282), diluted 1/5000 approximately in 50 mM TRIS-HCl buffer, pH 7.6.

After two rinses in PBS, the attachment of the antibodies is visualized by incubation under the same conditions of a goat anti-mouse IgG antibody conjugated with fluorescein isothianate (Biosys, FITC conjugated at 2 mg/ml) and diluted 1/150 in 50 mM TRIS-HCl buffer, pH 7.6. The reading is made under an optical microscope under UV light.

This monoclonal antibody was tested with respect to each of the isolates of the panel. It is attached exclusively to the CRFK cells infected with FCV 431.

This test may be used to determine the equivalents of the FCV 431 strain. These equivalents are those to which the monoclonal antibody 44 attaches.

Example 15

Cross-Serum Neutralization In Vitro

Cross-serum neutralization tests were carried out between 18 field isolates obtained by pharyngeal swabs performed on cats exhibiting signs of feline calicivirosis. 7 of them have as geographical origin France, they are the isolates identified A2, F3031, G1, G3, F1, H3-2 and H1-4. 4 have as geographical origin Great Britain, they are the isolates identified J5, 337, 388b and 431. Finally, 7 have as geographical origin the USA, they are the isolates identified RMI1, RMI2, RMI3, RMI5, RMI6, RMI7 and RMI9.

For each FCV virus, an antiserum was produced by inoculating kittens by the oronasal route with $10^{6.0}$ $CCID_{50}$ of the relevant FCV virus. The specific pathogen-free (SPF) kittens were 10 to 14 weeks old. The serum of each animal was collected one month after the infection. The sera were heat-inactivated (30 minutes at 56° C.), distributed, aliquoted and stored at −20° C.

The serum obtained for each isolate was tested for its ability to neutralize the 18 isolates. The sera were three-fold serially diluted with DMEM medium in 96-well cell culture plates. 0.05 ml of culture medium containing approximately 100 $CCID_{50}$ of the selected viral strain was added to 0.05 ml of the dilute serum. This mixture was incubated for 2 hours at 37° C. in an incubator under an atmosphere containing 5% $CO_2$.

0.15 ml of a suspension of CRFK cells containing about 100,000 cells per ml was then added to each mixture. The cytopathic effect was observed by phase contrast microscopy after 4 days of culture at 37° C. in an atmosphere containing 5% $CO_2$. The neutralizing titers of each serum were calculated according to the Kärber method. The titers are given in the form of the highest dilution inhibiting the cytopathic effect for 50% of the wells. The titers are expressed in $\log_{10}$. The minimum titer thus found was 0.7 $\log_{10}$ $VN_{50}$. Each serum was titrated at least twice, preferably three times.

FIG. 9 gives all the neutralizing titers obtained during cross-serum neutralizations carried out between these 18 FCV strains and these 18 sera.

It should be clearly understood that the invention defined by the appended claims is not limited to the specific embodiments indicated in the description above, but encompasses the variants which do not depart from the scope or the spirit of the present invention.

---

What is claimed is:

1. An isolated nucleic acid molecule comprising the nucleotide sequence represented in SEQ ID NO: 1 (FCV G1 capsid).

2. An isolated nucleic acid molecule encoding the capsid protein represented in SEQ ID NO: 2.

3. An in vivo or in vitro expression vector that comprises and expresses the isolated nucleic acid molecule according to claim 1.

4. The expression vector according to claim 3, wherein the vector is selected from the group consisting of a poxvirus, an adenovirus and a herpesvirus.

5. The expression vector according to claim 3, characterized in that it is a plasmid.

6. The expression vector according to claim 3 which further comprises and expresses a nucleotide sequence of an immunogen of an additional feline pathogen, or an epitope thereof.

7. The expression vector according to claim 6, wherein the additional feline pathogen is selected from the group consisting of the feline rhinotrachitis virus, feline herpesvirus (FHV), the feline leukemia virus(FeLV), the feline parvoviruses (FPV), the feline infectious peritonitis virus (FIPV), the feline immunodeficiency virus (FIV), the rabies virus, and *Chlamydia*.

8. An immunogenic preparation or vaccine comprising a veterinarily acceptable vehicle or excipient, an adjuvant, and a vector that contains and expresses in vivo at least one nucleic acid molecule, wherein the at least one nucleic acid molecule:
   (a) is a nucleic acid molecule having a sequence as claimed in claim 1, or
   (b) is a nucleic acid molecule having a sequence as claimed in claim 2, or
   (c) is a nucleic acid molecule having the nucleotide sequence represented in SEQ ID NO: 3 or a fragment of this sequence encoding an epitope, or
   (d) is a nucleic acid molecule encoding the capsid protein represented in SEQ ID NO: 4 or a fragment of this protein which is an epitope, or
   (e) comprises a nucleic acid as in (a) and a nucleic acid as in (c), or
   (f) comprises a nucleic acid as in (b) and a nucleic acid as in (d).

9. The immunogenic preparation or vaccine of claim 8 further comprising an in vivo expression vector into which a sequence encoding an immunogen of another feline pathogen is inserted.

10. A multivalent immunogenic preparation or vaccine against feline calicivirus and against at least one other feline pathogen, characterized in that it comprises an in vivo expression vector according to claim 6 and a veterinarily acceptable vehicle or excipient, and optionally an adjuvant.

11. An in vivo or in vitro expression vector comprising the nucleic acid molecule according to claim 2.

12. The expression vector of claim 11 selected from the group consisting of poxviruses, adenoviruses and herpesviruses.

13. The expression vector of claim 11 characterized in that it is a plasmid.

14. The immunogenic preparation or vaccine according to claim 8, wherein the vector is a plasmid and the adjuvant is a cationic lipid containing a quaternary ammonium salt of the formula $R_1OCH_2CH(OR_1)CH_2N^+(CH_3)_2(R_2)X$
   wherein $R_1$ is a saturated or unsaturated linear aliphatic radical having from 12 to 18 carbon atoms, $R_2$ is another aliphatic radical containing 2 or 3 carbon atoms, and X is a hydroxyl or amine group.

15. The immunogenic preparation or vaccine of claim 14, wherein the adjuvant is N-(2-hydroxyethyl)-N,N-dimethyl-2,3-bis(tetradecyloxy)-1-propane ammonium (DMRIE) optionally coupled with a neutral lipid dioleoyl-phosphatidyl-ethanol amine (DOPE) to form DMRIE-DOPE.

16. The immunogenic preparation or vaccine of claim 8, wherein at least one of the vectors is a poxvirus or canarypox virus and the adjuvant is a polymer of acrylic or methacrylic acid or a carbomer.

17. The immunogenic preparation or vaccine of claim 8, wherein it additionally comprises an in vivo expression plasmid vector into which the gene encoding feline granulocyte macrophage-colony stimulating factor (GM-CSF) is inserted.

18. An immunogenic preparation or vaccine comprising a veterinarily acceptable vehicle or excipient, an adjuvant, and a vector that contains and expresses in vivo a nucleic acid molecule having the nucleotide sequence represented in SEQ ID NO: 3 or a fragment of this sequence encoding an epitope.

19. The immunogenic preparation or vaccine according to claim 18, wherein the vector is a plasmid and the adjuvant is a cationic lipid containing a quaternary ammonium salt of the formula $R_1OCH_2CH(OR_1)CH_2N^+(CH_3)_2(R_2)X$
   wherein $R_1$ is a saturated or unsaturated linear aliphatic radical having from 12 to 18 carbon atoms, $R_2$ is another aliphatic radical containing 2 or 3 carbon atoms, and X is a hydroxyl or amine group.

20. The immunogenic preparation or vaccine of claim 19, wherein the adjuvant is DMRIE optionally coupled with a neutral lipid DOPE to form DMRIE-DOPE.

21. The immunogenic preparation or vaccine of claim 18, wherein at least one of the vectors is a poxvirus or canarypox virus and the adjuvant is a polymer of acrylic or methacrylic acid or a carbomer.

22. The immunogenic preparation or vaccine of claim 18, wherein it additionally comprises an in vivo expression plasmid vector into which the gene encoding feline GM-CSF is inserted.

23. An immunogenic preparation or vaccine comprising a veterinarily acceptable vehicle or excipient, optionally an adjuvant, a first vector that contains and expresses in vivo a nucleic acid molecule having a sequence as claimed in claim 1 and a second vector that contains and expresses in vivo a nucleic acid molecule having the nucleotide sequence represented in SEQ ID NO: 3 or a fragment of this sequence encoding an epitope.

24. An immunogenic preparation or vaccine comprising a veterinarily acceptable vehicle or excipient, optionally an adjuvant, a first vector that contains and expresses in vivo a nucleic acid molecule having a sequence as claimed in claim 2 and a second vector that contains and expresses in vivo a nucleic acid molecule having the nucleotide sequence represented in SEQ ID NO: 3 or a fragment of this sequence encoding an epitope.

* * * * *

UNITED STATES PATENT AND TRADEMARK OFFICE
CERTIFICATE OF CORRECTION

PATENT NO. : 6,914,134 B2
DATED : July 5, 2005
INVENTOR(S) : Jean-Christophe Francis Audonnet et al.

It is certified that error appears in the above-identified patent and that said Letters Patent is hereby corrected as shown below:

Title page,
Item [74], *Attorney, Agent, or Firm*, replace "Frommer Lawrence & Hang" with
-- Frommer Lawrence & Haug --.

Signed and Sealed this

Seventh Day of February, 2006

JON W. DUDAS
*Director of the United States Patent and Trademark Office*